United States Patent [19]

Teng et al.

[11] 4,454,363

[45] Jun. 12, 1984

[54] PROCESS FOR PREPARING INORGANIC METAL OXYGEN COMPOSITION CAPABLE OF DEHYDROCOUPLING TOLUENE

[75] Inventors: Harry H. Teng, Waldwick; I-Der Huang, Upper Saddle River; Hsuan L. Labowsky, Wayne, all of N.J.

[73] Assignee: Exxon Research & Engineering Co., Florham Park, N.J.

[21] Appl. No.: 387,693

[22] Filed: Jun. 11, 1982

[51] Int. Cl.$^3$ .......................... C07C 3/02; C07C 3/20
[52] U.S. Cl. .................................. 585/428; 585/435; 585/436; 585/440; 502/102; 502/340; 502/344; 502/349; 502/353
[58] Field of Search ............... 585/428, 429, 435, 436, 585/440; 252/461

[56] References Cited

U.S. PATENT DOCUMENTS

| | | | |
|---|---|---|---|
| 3,963,793 | 6/1976 | Weterings | 585/436 |
| 4,091,044 | 5/1978 | Li | 585/428 |
| 4,243,825 | 1/1981 | Williamson et al. | 585/428 |
| 4,254,293 | 3/1981 | Tremont et al. | 585/428 |
| 4,255,602 | 3/1981 | Tremont et al. | 585/428 |
| 4,255,603 | 3/1981 | Williamson et al. | 585/428 |
| 4,278,825 | 7/1981 | Tremont et al. | 585/428 |
| 4,278,826 | 7/1981 | Tremont et al. | 585/428 |

FOREIGN PATENT DOCUMENTS

| | | | |
|---|---|---|---|
| 1259766 | 1/1972 | United Kingdom | 585/428 |
| 1538670 | 1/1979 | United Kingdom | 585/428 |

OTHER PUBLICATIONS

Kirk-Othmer, Encyclopedia of Chemical Technology, vol. 3, (1978), p. 108.
Kirk-Othmer, Encyclopedia of Chemical Technology, vol. 22, (1970), pp. 606, 607, 609, 613.
Kirk-Othmer, Encyclopedia of Chemical Technology, vol. 14, (1981), pp. 164–165.

*Primary Examiner*—Delbert E. Gantz
*Assistant Examiner*—A. Pal
*Attorney, Agent, or Firm*—R. A. Maggio

[57] ABSTRACT

A process for preparing a metal oxygen composition capable of dehydrocoupling toluene wherein metal oxides such as $Sb_2O_3$, PbO, and $Bi_2O_3$ are admixed with an organic media such as isobutanol and heated to form a metal oxygen precursor composition which is recovered and calcined is disclosed.

88 Claims, No Drawings

PROCESS FOR PREPARING INORGANIC METAL OXYGEN COMPOSITION CAPABLE OF DEHYDROCOUPLING TOLUENE

BACKGROUND OF THE INVENTION

The present invention is directed to a process for preparing a metal/oxygen composition which composition is capable of dehydrocoupling toluene to stilbene.

Styrene is currently commercially produced from benzene in a two-step process. In the first step benzene is alkylated with ethylene to form ethylbenzene, and in the second step, the ethylbenzene is dehydrogenated to form styrene.

One of the known alternative routes for forming styrene involves the oxidative coupling of toluene to form 1, 2-diphenyl ethylene (stilbene) followed by the disproportionation of the stilbene with ethylene in the presence of a catalyst to form styrene. The economic significance of the overall process scheme of the toluene-stilbene route is that styrene can be produced from 0.5 mole of ethylene and one mole of toluene. This compared with the conventional ethylbenzene route wherein styrene is produced from one mole of ethylene and one mole of benzene. In light of the rising costs of benzene and ethylene and the environmental problems of benzene, the toluene-based process will become a more attractive route than the existing benzene-based process for styrene manufacture.

In addition to its utility as an intermediate in production of styrene, stilbene, because of its unsaturated character, is very reactive and may be employed in various organic syntheses. Derivatives of stilbene are useful in the production of chemicals which may be used in the manufacture of dyes, paints, and resins. It is also useful in optical brighteners, in pharmaceuticals and as an organic intermediate.

Thus, there is substantial economic incentive to develop an economical process for producing stilbene.

The oxidative coupling of toluene to 1,2-diphenyl ethane (i.e., bibenzyl) and stilbene has been known for many years.

The ideal reaction to stilbene from toluene is the direct dehydrocoupling reaction summarized as follows:

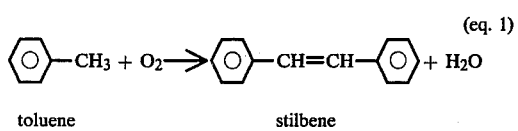

toluene     stilbene     (eq. 1)

Such a selective reaction in practice is difficult to achieve. More often, the overall reaction involves the dehydrocoupling of toluene to stilbene as well as bibenzyl. Bibenzyl however can be dehydrogenated to stilbene. Thus, a commercial process for producing stilbene could include an overall reaction scheme summarized as follows:

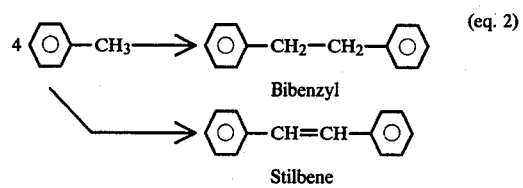

(eq. 2)

although the greater selectivity of the reaction to stilbene, the more efficient the process.

The reaction of Equation 1, employing oxygen as the oxidant in the absence of a catalyst, is extremely inefficient because of the preponderance of non-selective free-radical reactions leading to complete combustion of the hydrocarbons and the formation of oxygenated by-products. Consequently, attempts have been made to improve the selectivity of the reaction using oxidants, such as metal or non-metal oxides as stoichiometric reactants providing lattice oxygen which is depleted during the reaction. Such metal oxides can also function as catalysts for a primary oxidant such as oxygen. Because of the oxygen depletion of metal oxide stoichiometric oxidants, their use requires that they be either very inexpensive and therefore disposable, or they must be capable of being regenerated by replacing the lattice oxygen lost during the reaction. Since many of the conventional stoichiometric metal oxide oxidants are expensive, their use requires extensive plant equipment and engineering design to provide proper regeneration. This has led to two alternative approaches; namely, fixed bed and fluidized bed systems. In the fixed bed system, two or three reactors with staggered cycles typically are employed to achieve continuous operation. This system is very costly in terms of plant equipment. In the fluidized system a single reactor can be employed and a portion of the metal-oxide can be constantly removed, regenerated, and returned to the reactor. Fluidized systems, however, lead to attrition of the metal oxide and in many instances the metal of the metal oxide can be lost as fines which coat the walls of the reactors.

Another difficulty with stoichiometric oxidants and/or catalysts is that those producing relatively good selectivity usually result in a slow reaction rate. In addition the oxygen-carrying capacity is usually very low leading to a short active life.

Representative examples of conventional metal oxide oxidants and/or catalysts are disclosed in U.S. Pat. Nos. 3,694,518; 3,739,038; 3,868,427; 3,965,206; 3,980,580; 4,091,044; 4,183,828; 4,243,825; 4,247,727; 4,254,293; 4,255,602; 4,255,603; 4,255,604; 4,268,703; 4,268,704; 4,278,824; 4,278,825; and 4,278,826. These patents disclose various metal/oxide compositions which can be prepared by a variety of methods. For example, the simplest method involves intimately mixing the powdered metal oxides in the dry state and calcining. Another method involves adding the metal oxides to water with stirring, filtering to remove excess water or, alternatively, heating to evaporate the water, drying, and calcining. In another method of preparation, the powdered metal oxides can be intimately mixed before forming a paste with water and further mixing the paste. The paste can be dried in air, after which it can be calcined in air. The calcined product can then be crushed and sieved to the desired mesh size. In still another method of preparation, the powdered metal oxides can be mixed in the dry state together. A further method of preparation involves intimately mixing the powdered metal oxides in water and spray drying the resulting slurry or solution to produce relatively dust-free and free-flowing spherical particles which are also calcined prior to use. In an alternative method of preparation, suitable inorganic metal/oxygen composition precursor salts such as nitrates, carbonates, and acetates are intimately mixed or dissolved in water or nitric acid and heated to thermally decompose the precursor salts to form the corresponding oxides and/or oxygen complexes. The oxides and/or oxygen complexes can then be treated as described hereinabove prior to use.

Thus, a majority of these preparative methods employ water and are referred to herein as aqueous preparations. None of these patents disclose the use of organic liquids to prepare the metal oxide compositions.

The metal oxide compositions disclosed in these patents prepared by an aqueous method exhibit an extremely short active life. For example, Example 6 in U.S. Pat. No. 4,091,044 illustrates the use of a Sb/Pb/Bi oxide oxidant prepared by the aqueous method. When run for 1 minute at 580° C. (run 3, Table 6) the conversion is 47.3% and a selectivity for cis and trans stilbene plus bibenzyl is 81.2%. However, after 7 minutes reaction time (run 6, Table 6) the conversion drops to 9.7% at a corresponding selectivity of 87.5%. The substantial drop in conversion over a period of 5 minutes indicates that the oxidant is quickly deactivated and implies that it is not an efficient oxygen carrier. It is for this reason that the oxidant is typically regenerated for 30 to 60 minutes after each one-minute run (see Example 1, lines 34 et. seq.). Thus, not only is the oxidant quickly deactivated but its regeneration time is also quite long.

It is known that vanadium phosphorus oxygen catalysts for the oxidation of hydrocarbons, e.g. butane, to form, for example, maleic anhydride, can be prepared using an organic medium, such as isobutanol, as illustrated by U.S. Pat. Nos. 3,864,280; 4,132,670 and commonly assigned U.S. patent application Ser. No. 326,543 filed Dec. 2, 1981. However these catalysts are not employed for the conversion of toluene to stilbene.

The search has therefore continued for metal oxide compositions for use in conjunction with the conversion of toluene by oxidative dehydrocoupling to stilbene which possess the characteristics of (1) high activity and selectivity to minimize toluene recycle and loss to undesired by-products, (2) high oxygen-carrying capacity, (3) high reoxidation or regeneration rate to minimize the amount of composition employed, (4) high attrition resistance under conditions of repeated oxidation and reduction, and (5) high reaction rate. The present invention was developed in response to this search.

SUMMARY OF THE INVENTION

In one aspect of the present invention there is provided a process for preparing a precursor metal oxygen composition capable of dehydrocoupling toluene when calcined which comprises:

(i) reacting a mixture of metal oxides in the presence of at least one organic media comprising at least one member selected from the group consisting of organic: alcohol, aldehyde, ketone, ether, amine, amide and thiol, to form a metal oxygen precursor composition the metals of said metal oxide mixture having (a) at least one member selected from the group consisting of Tl, Bi, Pb, Co, and Th and (b) at least one member selected from the group consisting ot Li, Na, K, Rb, Cs, Fr, Be, Mg, Ca, Sr, Ba, Ra, In, Tl, Ge, P, As, Sb, Ag, Au, Cu, Zn, Cd, Hg, Sc, Y, La, Ac, Ti, Zr, Hf, Nb, Ta, Mn, Tc, Re, Fe, Ru, Os, Rh, Ir, Ni, Pd, Pt, Ce, Pr, Nd, Pm, Sm, Eu, Gd, Tb, Py, Er, Tm, Yb, Lu, and U;

(ii) separating the precursor composition from the organic media.

In another aspect of the present invention there is provided a process for preparing a metal oxygen composition capable of dehydrocoupling toluene which comprises calcining the above described precursor metal oxygen composition.

In a further aspect of the present invention there is provided a process for dehydrocoupling toluene and/or toluene derivatives using the metal oxygen composition prepared by the aforedescribed process.

In still another aspect of the present invention there is provided a metal oxygen composition prepared by the aforedescribed process.

DESCRIPTION OF PREFERRED EMBODIMENTS

A majority of the metals employed to prepare the metal oxide composition capable of dehydrocoupling toluene to stilbene are conventional in the art. More specifically, the inorganic metal oxide composition prepared in accordance with the present invention comprises a material which can be represented by the empirical formula:

$$A_a B_b O_x \qquad (I)$$

wherein A is at least one metal selected from the group consisting of Tl, Bi, Pb, Co, and Th; and B at least one metal selected from the group consisting of Li, Na, K, Rb, Cs, and Fr of Group 1A (of the periodic chart) Be, Mg, Ca, Sr, Ba, and Ra of Group 2a; In, and Tl of Group 3a; Ge of Group 4a; P, As, and Sb, of Group 5A; Ag, Au, and Cu, of Group 1b; Zn, Cd, and Hg of Group 2b; Sc, Y, La, and Ac of Group 3b; Ti, Zr, and Hf of Group 4b; Nb and Ta of Group 5b; Mn, Tc, and Re of Group 7b; Fe, Ru, Os, Rh, Ir, Ni, Pd, and Pt of Group 8; Ce, Pr, Nd, Pm, Sm, Eu, Gd, Tb, Dy, Er, Tm, Yb, and Lu, of the Lanthanides or rare earths; and Th and U of the actinides. Also in formula I, "a" is a number of about 1, "b" is a number of about 0.01 to about 100, preferably from about 0.01 to 10, most preferably 0.1 to 10; and "x" is a number taken to satisfy the average valences of metals A and B in the oxidation states in which they exist in the composition.

It is to be understood that while the above formula I and formulae which follow hereinafter are referred to as empirical formulae, they are not considered to be empirical formulae in the conventional sense. The precise structure of the metal oxide catalysts of the present invention has not yet been determined and X in these formulae in fact has no fixed determinate value since it can vary widely depending on the various possible combinations within the cataystt. That there is oxygen present is known and the $O_x$ in these formulae is representative of this. However, these formulae are significant in that they represent the gram atom ratio of the metal components of the catalyst.

Subgeneric classes of suitable metal oxide compositions falling within the scope of formula I include those represented by the following empirical formulae:

$$A_f^1 B_g^1 O_x \qquad (II)$$

wherein $A^1$ is Tl (of Group 3a); $B^1$ is at least one member selected from the group consisting of Sc, Y, La, Ac (of Group 3b); Ti, Zr, and Hf (of Group 4b); Nb, and Ta (of Group 5b); Mn, Tc, Re (of Group 7b); As and Sb (of Group 5a); Ce, Pr, Nd, Pm, Sm, Eu, Gd, Tb, Dy, Er, Tm, Yb, and Lu (of the Lanthanides or rare earths); Th, and U (of the actinides); preferably $B^1$ is selected from Ta, Sb, Ti, Zr, and Hf and mixtures; "a" is a number of about 1, "b" is a number of from about 0.01 to about 10; preferably from about 0.05 to about 5, and "x" is as described above;

$$A_h^2 B_j^2 O_x \quad (III)$$

wherein $A^2$ is Bi; $B^2$ is at least one member selected from the group consisting of Be, Mg, Ca, Sr, Ba, and Ra (of Group 2a); In (of Group 3a); Ag (of Group 1b); preferably $B^2$ is Ag, Mg, Ca, Sr or Ba and mixtures thereof; "h" is a number of about 1, "j" is a number of from about 0.01 to about 100, preferably from about 0.1 to about 10, and "x" is as described above;

$$A_k^3 B_l^3 O_x \quad (IV)$$

wherein $A^3$ is Bi; $B^3$ is at least one member selected from the group consisting of Li, Na, K, Rb, Cs, and Fr (of Group 1a); Sc, Y, La, and Ac (of Group 3b); Ti, Zr, and Hf (of Group 4b); Fe, Ru, Os, Co, Rh, Ir, Ni, Pd, and Pt (of Group 8); Zn (of Group 2b); Ge (of Group 4a); Ce, Pr, Nd, Pm, Sm, Eu, Gd, Tb, Dy, Er, Tm, Yb, and Lu (of the Lanthanides or rare earths); Th (of the actinides); preferably $B^3$ is selected from Zn, Ce, Li, Na, K, Cs, and Zr and mixtures; "k" is a number of about 1, "l" is a number of from about 0.01 to about 10, preferably from about 0.5 to about 5, and "x" is as described above;

$$A_m^4 B_n^4 O_x \quad (V)$$

wherein $A^4$ is cobalt; $B^4$ is La, "m" is a number of about 1, "b" is a number of from about 1 to about 10, preferably from about 1 to about 5, and "x" is as described above;

$$A_o^5 B_p^5 O_x \quad (VI)$$

wherein $A^5$ is Th; $B^5$ is at least one member selected from the group consisting of Cu (of Group 1b); Zn, Cd, and Hg (of Group 2b); preferably $B^5$ is Zn; "o" is a number of about 1, "p" is a number of from about 0.01 to about 10, preferably from about 0.5 to about 5; and "x" is as described above;

$$A_g^6 B_r^6 O_x \quad (VII)$$

wherein $A^6$ is Pb; $B^6$ is at least one member selected from the group consisting of Li, Na, K, Rb, Cs, Fr (of Group 1a); Sc, Y, La, and Ac (of Group 3b); Ti, Zr, and Hf (of Group 4b); Fe, Ru, Os, Co, Rh, Ir, Ni, Pd, and Pt (of Group 8), Ag (of Group 1b); Zn (of Group 2b); Ge (of Group 4a), P and As (of Group 5a); Ce, Pr, Nd, Pm, Sm, Eu, Gd, Tb, Py, Er, Tm, Yb, and Lu (of the Lanthanides or rare earths); Th (of the actinides); (preferably $B^6$ is selected from Ag, Zn, As, Li, Na, K, Rb, Cs, Zr, and mixtures, most preferably Ag, Zn, K, and Zr); "g" is a numer of about 1, "r" is a number of from about 0.01 to about 10, preferably from about 0.5 to about 5, and "x" is as described above;

$$A_s^7 B_t^7 O_x \quad (VIII)$$

wherein $A^7$ is Pb; $B^7$ is at least one member selected from the group consisting of Be, Mg, Ca, Sr, Ba, Ra (of Group 2a); Tl (of Group 3a) (preferably $B^7$ is selected from Ba, Ca, Sr and mixtures); "s" is a number of about 1; "t" is a number of from about 0.01 to about 10, preferably from about 0.5 to about 5; and "x" is as described above;

$$Sb_c Pb_d Bi_e O_x \quad (IX)$$

wherein "c" is a number of about 1, "d" is a number of from about 0.1 to about 10, preferably from about 0.5 to about 5, "e" is a number of from 0 to about 5, preferably from about 0 to about 1, and "x" is as defined in connection with formula I as it pertains to the oxidation state of Sb, Pb, and Bi metals in the formula; and $$D_u E_v Sb_y Bi_z O_x \quad (X)$$

wherein D is at least one member selected from the group consisting of Li, Na, K, Rb, Cs, Fr, Be, Mg, Ca, Sr, Ba, and Ra; preferably D is Cs; E is at least one member selected from the group consisting of Pb, Au, Ag, Pt, Pd, Cu, Zn, Cd, and Hg; preferably E is Pb, Au, or Cu; most preferably Cu; "u" is a number which can vary from about 0 to about 10, preferably from about 0.5 to about 5; "v" is a number which can vary from about 0 to about 10, preferably from about 0.5 to about 5; "y" is a number which can vary from about 0 to about 10, preferably from about 0.5 to about 5; "z" is a number which can vary from about 0.01 to about 10, preferably from about 0.01 to about 5; and "x" is as defined in connection with formula I as it pertains to the oxidation state of D, E, Sb, and Bi.

Representative examples of empirical formulas (based on formula I) of metal oxygen compositions which can be prepared in accordance with the present invention are described below. The letters "a" and "b" in each formula collectively represent the gram atom ratios of each metal in the composition. The letter "x" of each of these formulas is as described above is indeterminate although its theoretical value can be calculated from the representative oxidation states of each metal as also provided. Furthermore, the oxidation states of each of the metals of the calcined metal oxygen composition may vary between the highest and lowest possible oxidation states in a single composition.

| Empirical Formula | a | b |
|---|---|---|
| $Tl_a^{+3} Sb_b^{+3} O_x$ | 1 | .3 |
| " | 1 | .5 |
| " | 1 | 1 |
| " | 1 | 2 |
| " | 1 | 3 |
| $Tl_a^{+3} Ti_b^{+4} O_x$ | 1 | .2 |
| " | 1 | .3 |
| " | 1 | .5 |
| " | 1 | 1 |
| " | 1 | 2 |
| " | 1 | 3 |
| $Tl_a^{+3} Ta_b^{+5} O_x$ | 1 | 1 |
| $Tl_a^{+3} Mn_b^{+2} O_x$ | 1 | 1 |
| $Tl_a^{+3} La_b^{+3} O_x$ | 1 | 1 |
| $Tl_a^{+3} U_b^{+5} O_x$ | 1 | 1.5 |
| $Bi_a^{+3} Ca_b^{+2} O_x$ | 1 | 0.1 |
| " | 1 | 0.3 |
| " | 1 | 0.5 |
| " | 1 | 1 |
| " | 1 | 2 |
| " | 1 | 10 |

| Empirical Formula | a | b |
|---|---|---|
| " | 1 | 100 |
| $Bi_a^{+3}Sr_b^{+2}O_x$ | 1 | .3 |
| " | 1 | .5 |
| " | 1 | 1 |
| " | 1 | 4 |
| $Bi_a^{+3}In_b^{+3}O_x$ | 1 | 1 |
| $Bi_a^{+3}Ag_b^{+1}O_x$ | 1 | .1 |
| " | 1 | .16 |
| " | 1 | .2 |
| " | 1 | .3 |
| " | 1 | .5 |
| $Bi_a^{+3}Ca_b^{+2}Ag_b^{+1}O_x$ | 1 | .3 |
| $Bi_a^{+3}Ca_b^{+2}In_b^{+3}O_x$ | 1 | Ca = .3, In = .8 |
| $Bi_a^{+3}Ca_b^{+2}Sr_b^{+2}O_x$ | 1 | .5 |
| $Pb_a^{+2}Sr_b^{+2}O_x$ | 1 | .1 |
| " | 1 | .3 |
| " | 1 | .5 |
| " | 1 | 1 |
| " | 1 | 2 |
| " | 1 | 3 |
| $Pb_a^{+2}Mg_b^{+2}O_x$ | 1 | 1 |
| $Pb_a^{+2}Ba_b^{+2}O_x$ | 1 | 1 |
| $Pb_a^{+2}Tl_b^{+3}O_x$ | 1 | 2 |
| $Bi_a^{+3}Zn_b^{+2}O_x$ | 1 | .1 |
| " | 1 | .17 |
| " | 1 | .25 |
| " | 1 | .5 |
| " | 1 | 1 |
| " | 1 | 2 |
| " | 1 | 3 |
| $Bi_a^{+3}K_b^{+1}O_x$ | 1 | .013 |
| " | 1 | .21 |
| " | 1 | .43 |
| " | 1 | 1 |
| $Bi_a^{+3}Ni_b^{+2}O_x$ | 1 | .2 |
| " | 1 | .3 |
| " | 1 | .5 |
| " | 1 | 1 |
| " | 1 | 2 |
| " | 1 | 3 |
| $Bi_a^{+3}Zr_b^{+4}O_x$ | 1 | .17 |
| " | 1 | .3 |
| " | 1 | 1 |
| " | 1 | 2 |
| " | 1 | 3 |
| $Bi_a^{+3}Ge_b^{+4}O_x$ | 1 | .17 |
| " | 1 | .7 |
| " | 1 | 3.8 |
| $Bi_a^{+3}Ce_b^{+4}O_x$ | 1 | .17 |
| " | 1 | .33 |
| " | 1 | .5 |
| " | 1 | 1 |
| " | 1 | 2 |
| " | 1 | 3 |
| $Bi_a^{+3}La_b^{+3}O_x$ | 1 | .3 |
| " | 1 | .5 |
| " | 1 | 1 |
| " | 1 | 1 |
| " | 1 | 2 |
| " | 1 | 3 |
| $Bi_a^{+3}Th_b^{+4}O_x$ | 1 | .3 |
| " | 1 | .5 |
| " | 1 | 1 |
| " | 1 | 2 |
| " | 1 | 3 |
| $Bi_a^{+3}Th_b^{+4}Zn_b^{+2}O_x$ | 1 | Th = .16, Zn = .5 |
| $Bi_a^{+3}La_b^{+3}K_b^{+1}O_x$ | 1 | La = 1, K = .5 |
| $Bi_a^{+3}Ge_b^{+4}Ni_b^{+2}O_x$ | 1 | Ge = .25, Ni = .5 |
| $Bi_a^{+3}Zn_b^{+2}Zr_b^{+4}O_x$ | 1 | Zn = 1, Zr = 1 |
| $Bi_a^{+3}Ce_b^{+4}Th_b^{+4}O_x$ | 1 | Ce = .2, Th = 1 |
| $Co_a^{+6}La_b^{+3}O_x$ | 1 | 1 |
| " | 1 | 2 |
| " | 1 | 3 |
| $Th_a^{+4}Zn_b^{+2}O_x$ | 1 | .3 |
| " | 1 | .5 |
| " | 1 | 1 |
| " | 1 | 2 |
| " | 1 | 3 |
| $Th_a^{+4}Cu_b^{+2}O_x$ | 1 | 1 |
| $Th_a^{+4}Cd_b^{+2}O_x$ | 1 | 1 |
| $Pb_a^{+2}Zr_b^{+4}O_x$ | 1 | .3 |

| Empirical Formula | a | b |
|---|---|---|
| " | 1 | .5 |
| " | 1 | 1 |
| " | 1 | 2 |
| " | 1 | 3 |
| $Pb_a^{+2}K_b^{+1}O_x$ | 1 | 2 |
| $Pb_a^{+2}Y_b^{+3}O_x$ | 1 | .3 |
| " | 1 | .5 |
| " | 1 | 1 |
| " | 1 | 6 |
| " | 1 | 10 |
| $Pb_a^{+2}Co_b^{+2}O_x$ | 1 | 1 |
| $Pb_a^{+2}Th_b^{+4}O_x$ | 1 | 1 |
| $Pb_a^{+2}Zn_b^{+2}O_x$ | 1 | .2 |
| " | 1 | .3 |
| " | 1 | .5 |
| " | 1 | 1 |
| " | 1 | 2 |
| " | 1 | 3 |
| " | 1 | 5 |
| $Pb_a^{+2}P_b^{+5}O_x$ | 1 | 1 |
| $Pb_a^{+2}As_b^{+5}O_x$ | 1 | 1 |
| $Pb_a^{+2}Ag_b^{+1}O_x$ | 1 | .1 |
| " | 1 | .13 |
| " | 1 | .17 |
| " | 1 | .25 |
| " | 1 | .5 |
| $Pb_a^{+2}Ag_b^{+1}Zr_b^{+4}O_x$ | 1 | Ag = .7, Zr = .3 |
| $Pb_a^{+2}K_b^{+1}Zr_b^{+4}O_x$ | 1 | K = .8, Zr = .3 |
| $Pb_a^{+2}Y_b^{+3}Zr_b^{+4}O_x$ | 1 | Y = .3, Zr = .35 |
| $Pb_a^{+2}Zn_b^{+2}Th_b^{+4}O_x$ | 1 | Zn = .4, Th = .01 |
| $Pb_a^{+2}Zn_b^{+2}Co_b^{+2}O_x$ | 1 | Zn = .3, Co = .17 |

Representative examples of empirical formulas of metal oxide compositions, based on formula IX, are illustrated below. In these formulas, the letters "c", "d" and "e" as provided collectively represent gram atom ratios of the respective metals. The letter "x" is as described above.

| Empirical Formula | c | d | e |
|---|---|---|---|
| $Sb_c^{+3}Pb_d^{+2}Bi_e^{+3}O_x$ | 1 | 1.5 | 0 |
| " | 1 | 2 | .25 |
| " | 1 | 2 | 0 |
| " | 1 | 3 | 0 |
| " | 1 | 4 | 0 |
| " | 1 | 5 | 0 |
| " | 1 | 1.5 | .25 |

Representative examples of empirical formulas of metal oxide compositions, based on structural formula X are illustrated below. In these formulas the letters "u", "v", "y" and "z", collectively represent gram atom ratios of the respective metals. The letter "x" is as described above.

| Empirical Formula | u | v | y | z |
|---|---|---|---|---|
| $Sb_yBi_zO_x$ | 0 | 0 | 1 | 1 |
| " | 0 | 0 | 0.25 | 1 |
| " | 0 | 0 | 1.0 | 0.25 |
| $Cs_uSb_yBi_zO_x$ | 0.05 | 0 | 1.0 | 0.25 |
| " | 0.1 | 0 | 1.0 | 0.25 |
| " | 0.5 | 0 | 1.0 | 0.25 |
| " | 1.0 | 0 | 1.0 | 0.25 |
| $Cs_uPb_vSb_yBi_zO_x$ | 0.05 | 1.5 | 1.0 | 0.25 |
| " | 0.1 | 1.5 | 1.0 | 0.25 |
| " | 0.5 | 1.5 | 1.0 | 0.25 |
| " | 1.0 | 1.5 | 1.0 | 0.25 |
| $Cu_vSb_yBi_zO_x$ | 0 | 0.25 | 1.0 | 0.25 |
| " | 0 | 0.5 | 1.0 | 0.25 |
| " | 0 | 0.5 | 1.0 | 0.5 |
| " | 0 | 0.5 | 0.5 | 1.0 |
| $Au_vSb_yBi_zO_x$ | 0 | 0.05 | 1.0 | 0.25 |
| " | 0 | 0.05 | 1.0 | 0.50 |

-continued

| Empirical Formula | u | v | y | z |
|---|---|---|---|---|
| " | 0 | 0.1 | 1.0 | 0.25 |
| " | 0 | 0.1 | 1.0 | 0.50 |
| $Cs_uCu_vSb_yBi_zO_x$ | 0.05 | 0.25 | 0 | 1.0 |
| " | 0.1 | 0.25 | 0 | 1.0 |
| " | 0.5 | 0.25 | 0 | 1.0 |
| " | 1.0 | 0.25 | 0 | 1.0 |
| $K_vSb_yBi_zO_x$ | 0 | 0.05 | 1.0 | 0.25 |
| " | 0 | 0.1 | 1.0 | 0.25 |
| " | 0 | 0.5 | 0 | 1.0 |
| " | 0 | 1.0 | 0 | 1.0 |
| $Rb_uAu_vSb_yBi_zO_x$ | 0.05 | 0.05 | 1.0 | 0.25 |
| " | 0.1 | 0.05 | 1.0 | 0.25 |
| " | 0.5 | 0.05 | 1.0 | 0.25 |
| " | 1.0 | 0.05 | 1.0 | 0.25 |

Representative starting materials in metal oxide form, from which the metal oxide composition of the present invention can be prepared include $Sb_2O_3$, $PbO$, $Bi_2O_3$, $Tl_2O_3$, $Ta_2O_5$, $La_2O_3$, $Tl_2O_3$, $U_3O_8$, $CaO$, $In_2O_3$, $SrO$, $BaO$, $MgO$, $ZnO$, $ZrO_2$, $GeO_3$, $CeO_2$, $Y_2O_3$.

However, included within the term metal oxides are precursors of said metal oxides such as nitrates, carbonates, and acetates which can be converted to their corresponding metal oxides by heat treatment.

Representative illustrations of such precursor metal oxides include $Mn(NO_3)_2$, $Bi(NO_3)_3$, $AgNO_3$, $Th(NO_3)_4$, $CoCO_3$, $Zn(NO_3)_2$, $Cu(NO_3)_2$, $NaHCO_3$, $Na_2CO_3$.

The process for preparing the metal oxide compositions of the present invention is conducted by reacting at least two of the oxides of said metals in the presence of at least one organic media, e.g., alcohol, under conditions and in a manner sufficient to form a catalyst precursor composition. The term "media" is used herein in a collective sense to signify singular and/or plural.

When an alcohol is employed as the liquid organic media, water and other organic by-products, such as ethers, esters and the like, are formed as a result of this reaction and there are essentially no other detectable by-products therefrom. While not wishing to be bound by any particular theory, this occurence has led to the conclusion that the organic alcohol participates in this reaction, although to an undetermined extent, through the hydroxy functional group thereby releasing water. More specifically, it is further believed that the alcohol may react with at least the surface of the metal oxide particles to form an alkoxide which in turn may become an active intermediate for further reaction to form the complex metal oxide catalyst matrix. An organic media with reducing properties may facilitate this intermediate forming reaction.

In any event, the metal oxides are eventually reacted with each other and the precursor catalyst composition is not believed to be a mere mixture of oxides.

The above reaction can be conducted by admixing at least two of said metal oxides with at least one organic media and heating the admixture. Since most metal oxides are generally at least partially insoluble in the organic media, a slurry or suspension will result and the reaction is conducted in a heterogeneous phase. However, an organic media which dissolves the metal oxides can also be employed although this complicates the recovery procedure. Accordingly, it is contemplated to employ organic metal oxides such as antimony butoxide and magnesium methoxide which are soluble in the organic media, as starting materials in the process of the present invention.

Thus, the organic media functions as a solvent and/or suspending medium for the metal oxides, as a solvent and/or suspending agent for the catalyst precursor composition, as a medium for providing uniform heating of the metal oxides, and optionally as a reactant.

The organic media is comprised of carbon, hydrogen, and at least one hetero-atom such as oxygen, nitrogen or sulfur.

Included within the scope of organic media are alcohols, aldehydes, ketones, ethers, amines, amides, and thiols, and mixtures thereof, containing typically from about 1 to about 20, preferably from about 1 to about 10, and most preferably from about 1 to about 5 carbon atoms.

More specifically, the organic moiety to which the alcohol, aldehyde, ketone, ether, amine, amide, and thiol functional groups can be attached includes alkyl, typically about $C_1$ to about $C_{20}$, preferably $C_1$ to $C_{10}$, most preferably $C_1$ to $C_5$ alkyl; aryl, typically about $C_6$ to about $C_{14}$, preferably about $C_6$ to about $C_{10}$, most preferably $C_6$ aryl, cycloalkyl, typically about $C_4$ to about $C_{20}$, preferably about $C_6$ to about $C_{12}$, most preferably about $C_6$ to $C_{10}$ cycloalkyl, aralkyl and alkaryl wherein the alkyl and aryl groups thereof are described above.

Each class of liquid organic media can contain one or more, typically 1 to 3, functional groups.

The preferred organic compounds are the primary and secondary alcohols. Alcohols which contain 1, 2 or 3 hydroxyl substituent groups are especially preferred because these, in general, are readily liquified at useful temperatures in the process range. Representative hydroxylic compounds useful in the process include monoalcohols, such as methanol, ethanol, isopropanol, 1-propanol, 1-butanol, isobutanol, 2-butanol, t-butanol, 1-pentanol, cyclohexanol, 1-octanol, 2-octanol, 3-octanol, 4-octanol, 2-hexadecanol, 2-eicosanol, 2-ethyl-1-hexanol, phenol, benzyl alcohol, etc.; di-alcohols, such as ethylene glycol, 1,4-butanediol, 1,2-propanediol; trialcohol such as glycerine, 2,2-dimethylol-1-propanol; ether alcohols such as diethylene glycol, triethylene glycol, 2-butoxyethanol, 4-methoxybutanol, tetrahydrofurfuryl alcohol; and mixtures thereof.

Representative aldehydes include benzaldehyde, formaldehyde, acetaldehyde, propionaldehyde, m-tolualdehyde, 2-ethylhexanol, trioxane, valeraldehyde and mixtures thereof.

Representative ketones include acetone, methylethylketone, cyclohexanone, dimethyl ketone, diethyl ketone, dibutyl ketone, methyl isopropyl ketone, methyl sec butyl ketone, benzophenone, and mixtures thereof.

Representative ethers include diethyl ether, dibutyl ether, tetrahydrofuran, anisole, dioctyl ether, 1,2-dimethoxyethane, 1,4-dimethoxybutane, diethylene, ether, and mixtures thereof.

Representative amines include ethylene diamine, hexylamine, cyclohexyl amine, diethylamine, 1,3-butadiamine, ethylene triamine, n-phenylbenzamine and mixtures thereof.

Representative amides include formamide, dimethyl formamide, acetamide, 3-butaneamide, n-phenyl acetamide, azacyclohexan-2-one, hexanediamide and mixtures thereof.

Representative thiols include phenylmethanethiol, ethanethiol, pentanethiol, 1,4-butanedithiol, cyclohexanethiol, benzylthiol, 1,5-pentane dithiol; and mixtures thereof.

The primary and secondary alkanols (ROH) having a carbon atom content in the range from 3 to 6 are a preferred class of liquid organic media for reason of cost and availability and because of their convenient boiling points. Isobutanol is the optimum liquid.

In short, any of the aforenoted organic compounds alone or in any combination can be employed as the organic media.

The organic media may also contain non-oxygenated unreactive diluents which are in the liquid phase at reaction temperature. These include hydrocarbons, mono- and polychlorinated hydrocarbons, and the like diluents.

The diluents which can be most advantageously employed are less expensive than the organic media and help to reduce the cost of the overall process. However, a minimum amount of hetero-atom containing organic media is employed as described herein to form the precursor composition.

Representative compounds which can function as a diluent in the organic media include hexane, heptane, octane, cyclohexane, methylcyclopentane, 2,2,4-trimethylpentane, dodecane, 2- ethylhexane, 3-octene, cyclohexene; benzene, toluene, o-xylene, m-xylene, p-xylene, ethylbenzene, trimethylbenzene, 2-propylbenzene; methylene chloride, chloroform, carbon tetrabromide, carbon tetrachloride 3-chlorohexane, 2,3-dichlorooctane, chlorocyclohexane, 1,2-dichloropentane, 1,2-dichloroheptane, 1,1,2-trichloroethane; chlorobenzene, bromobenzene, o-dichlorobenzene, p-dichlorobenzene, 2-chlorotoluene, 4-chlorotoluene, 2,4-dichlorotoluene, 1,3-dimethyl-4-chlorobenzene, butyl bromide, and the like hydrocarbons and halogenated hydrocarbons.

The proportion of each metal oxide added to the reaction mixture is selected to achieve the gram atom metal ratios employed to yield a metal oxygen composition capable of dehydrocoupling toluene such as described above in the final composition in conjunction with the aforementioned formulas I and II.

The amount of organic media which is admixed with the metal oxides in any amount sufficient to permit uniform heating and mixing of the reaction mixture and formation of the precursor composition. Generally, the number of moles of organic media is at least equal to the sum of the number of moles of each metal in the metal oxide mixture multiplied by the oxidation state of each metal in said mixture. Thus, while any effective amount of organic media can be employed, such effective amounts will constitute a ratio of moles of metal in the metal oxide mixture per mole of organic media of typically at least 1:1, preferably at least 1:3, and most preferably at least 1:8. The preferred amount of organic media is calculted according to the formula:

Moles of organic media $= \Sigma_i M_i \times V_{max,i}$ wherein $M_i$ is the moles of ith metal in the catalyst system and $V_{max,i}$ is the maximum possible oxidation state of metal M. Most preferably about 5 to about 10 times the moles of organic media calculated from the above equation is employed initially and the excess over the calculated quantity is gradually removed.

Alternatively, the amount of organic media and metal oxides can be expressed as a percentage of the reaction mixture. Thus, the reaction mixture will comprise typically from about 1 to about 60%, preferably from about 10 to about 50%, and most preferably from about 10 to about 30%, by weight, metal oxides, and typically from about 40 to about 99%, preferably from about 50 to about 90%, and most preferably from about 70 to about 90%, by weight, organic media, based on the weight of the reaction mixture.

The reaction mixture comprising organic media and metal oxides is heated to any temperature sufficient to form the precursor composition. Thus, while any effective temperature may be employed, such effective temperatures typically will be at least 20° C., preferably at least 75° C., and most preferably at least 105° C., and can vary typically from about 20° to about 200° C., preferably from about 75° to about 150° C., and most preferably from about 100° to about 110° C.

Preferably, the organic media is selected so that it will boil at the selected reaction temperature. This permits refluxing of the reaction mixture.

During heating of the reaction mixture, any water and/or volatile organic by-products such as esters, ethers, aldehydes, ketones and acids formed in-situ are preferably removed, for example, by azeotropic distillation. Thus, the reaction mixture is preferably heated under substantially anhydrous conditions.

By "substantially anhydrous" as used herein is meant typically less than about 10%, preferably less than about 5%, and most preferably less than about 1%, by weight water, based on the weight of the organic media in the reaction mixture.

As stated above, the reaction mixture typically will exist as a slurry of suspended material during heating.

The term "slurry" as used in connection with the catalyst precursor forming step is defined herein to mean a suspension wherein the solid components thereof are present therein at a solids content of typically not greater than about 60, preferably not greater than about 40, and most preferably not greater than about 25%, by weight, based on the weight of the suspension.

The order of addition of the metal oxides to the organic media is not critical.

The reaction time is selected in conjunction with the reaction temperature to permit substantially complete reaction at the above reaction temperatures. Such reaction times typically will vary from about 2 to about 48 hours, preferably from about 10 to about 30 hours, and most preferably from about 16 to about 24 hours.

Upon completion of the reaction, the precursor composition is separated from the reaction mixture by any means capable of achieving this goal. Since the precursor composition typically is insoluble in the reaction mixture, bulk separation can be accomplished by simple filtration techniques. Alternately, the residual organic media can be distilled to form a wet paste. Residual liquid is preferably removed from the filtrand (i.e., the insoluble material removed from the filtrate) or paste by drying the same, typically at temperatures of from about 25 to about 210° C., preferably from about 80° to 160° C., and most preferably from about 100° to about 150° C.

The isolated precursor composition is then calcined to form the metal oxygen composition capable of dehydrocoupling toluene. Calcination can be conducted in a separate step or in-situ in the reactor and involves heating the metal oxygen composition to at least reaction temperature.

Accordingly, calcination is conducted at temperatures of typically from about 300° to about 1200° C., preferably from about 400° to about 1000° C. (e.g. 500° to 1000° C.), and most preferably from about 600° to about 900° C. for a period of typically from about 0.5 to about 24 hours, preferably from about 1 to about 10 hours, and most preferably from about 1 to about 4 hours.

The atmosphere under which calcination is conducted is capable of oxidizing, where possible, the metal(s) in the metal oxygen composition. Such atmospheres include oxygen or an oxygen containing gas such as air; a gaseous mixture of air and minor amounts of at least one of the inert gases such as helium, argon and the like; and a mixture of air and minor amounts of at least one other gas such as $CO_2$, $CO$, $H_2$, and hydrocarbon (e.g. toluene). The preferred calcination atmosphere is air. While the calcination atmosphere may be passed as a moving stream over the precursor composition, it is preferred that the calcination atmosphere be static in nature.

After calcination is conducted the metal oxygen composition can optionally be activated. Activation involves preconditioning the metal oxygen composition with air or other atmosphere described in connection with calcination before selecting the final operating conditions. Activation is therefore typically conducted by contacting the metal oxygen composition with said gaseous atmosphere at temperatures of typically from about 350 to about 700, preferably from about 400 to about 650, and most preferably from about 400° to about 600° C.

Activation times can vary typically from about 1 to about 24, preferably from about 2 to about 20, and most preferably from about 10 to about 16 hours. While activation may be conducted in a static atmosphere it is preferred that such atmosphere be dynamic and pass over the the catalyst as a fluid stream.

The attrition resistance of the metal oxide composition can be substantially improved by incorporating at least one: alkali or alkaline earth metal oxide, preferably alkali metal oxide, most preferably cesium oxide into the final composition. This can be achieved by selecting the appropriate alkali or alkaline earth metal oxide as one of the initial metal oxides which is admixed with the organic media. Alternatively, and most preferably, the appropriate metal oxide is impregnated into the precursor composition after removal of the organic media therefrom by any suitable method. In accordance with the preferred method of impregnation, the appropriate alkali or alkaline earth metal oxide is dissolved in water to form a solution, e.g., of $CsOH/H_2O$, and the precursor composition is admixed with the solution to form a slurry.

The resulting slurry is then stirred for a time of typically from about 1 to about 24, preferably from about 2 to 16, and most preferably from about 4 to about 10 hours, at temperatures of typically from about 25 to about 100, preferably from about 60 to about 80, and most preferably from about 65° to about 75° C. to effect impregnation.

The impregnated precursor composition solids are then recovered by, for example, evaporating the water to form a thick paste which is then dried in an oven at the aforedescribed drying temperatures. The impregnated precursor composition is then calcined as described herein.

The attrition resistance effect has been found to be imparted to the final composition by the alkali or alkaline earth metal oxide when present therein in amounts of typically from about 0.01 to about 100, preferably 0.1 to about 10, and most preferably from about 1.0 to about 5.0 mole % attrition resistance modifying metal, based on the total number of moles of metals in the metal oxygen composition.

The surface area of the metal oxide composition after calcination typically will vary from about 0.1 to about 10, preferably from about 0.1 to about 2.0, and most preferably from about 0.1 to about 1.0 $m^2/gm$, as determined by the B.E.T. method.

The metal oxide composition resulting after calcination exhibits improved activity and selectivity vis-a-vis the dehydrocoupling of toluene to stilbene relative to metal oxide composition derived from similar metal oxides prepared by prior art techniques, particularly the aqueous slurry techniques discussed above. In addition, the metal oxide composition of the present invention deactivates at a slower rate than those prepared by prior art techniques and is more attrition resistant. Thus, while the metal oxide composition of the present invention may possess an empirical formula similar to that of the prior art, the particular method of preparation described herein is believed to alter both the precursor and final composition's basic physical and/or chemical characteristics in terms of crystal structure, porosity and surface area relative to prior art compositions to the extent that improved effects are observed as described herein.

The inorganic metal oxygen composition of the present invention can function in a catalytic mode, a stoichiometric mode (also referred to herein as the cyclic mode because of the need for regeneration of lattice oxygen) as an oxidant or oxygen carrier, or a combined catalytic/stoichiometric mode for the dehydrocoupling of toluene.

In the catalytic mode of operation, oxygen or an oxygen-containing gas such as air or oxygen-enriched air is reacted with toluene in an amount sufficient for the dehydrocoupling reaction, said reaction being catalyzed by and conducted in the presence of the metal oxygen composition.

In the stoichiometric mode of operation, the metal oxygen composition is the sole source of oxygen. That is, in the latter instance the dehydrocoupling of toluene is conducted in the substantial absence of added free oxygen such as would be obtained from air. Consequently, the metal oxygen composition when operating in this mode is eventually depleted of oxygen and must be regenerated as described hereinafter.

In the combined catalytic/stoichiometric mode of operation, oxygen or an oxygen-containing gas is added as a reactant in a manner similar to that noted hereinabove for the catalytic mode of operation. However, the amount of added oxygen is not sufficient by itself to meet the stoichiometric oxygen requirements of the dehydrocoupling reaction. Consequently, additional oxygen must be applied by the inorganic metal oxygen composition. The amount of added free oxygen is typically controlled and limited by diluting the atmosphere in contact with the metal oxygen composition with a suitable inert gas such as nitrogen.

Of these three modes of operation, the stoichiometric mode is generally preferred although this preference may change depending on the particular metal oxygen composition selected.

The term "dehydrocoupling" and related terms are employed herein to mean that the toluene molecules are coupled or dimerized, with carbon-carbon bond formation occurring between the methyl group carbons, and the coupled molecules have lost either one or two hydrogen atoms from the methyl group of each toluene molecule. When two hydrogen atoms per molecule of toluene are lost, the carbon-carbon bond at the coupling or dimerization site is unsaturated as by dehydrogenation, that is, stilbene is the product. On the other hand, bibenzyl, having a saturated carbon-carbon bond at the coupling site, is the product when only one hydrogen atom per molecule of toluene is lost.

In general, the production of stilbene as the dehydrocoupled toluene product is preferred over the production of bibenzyl. This stated preference is due to the unsaturated character of stilbene as opposed to the saturated character of bibenzyl. As is well known is the art, the presence of the unsaturated olefinic carbon-carbon double bond causes the stilbene to exhibit high reactivity, thereby facilitating its direct use an an organic intermediate in numerous organic syntheses.

The process of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactant or reactants and metal oxygen composition. The reactant toluene or toluene derivatives will generally be heated and introduced into the reactor as a vapor. However, the reactant may be introduced to the reactor as a liquid and then vaporized.

The oxidative dehydrocoupling reaction is preferably carried out in the vapor phase and under the influence of heat. The temperature range under which the reaction can be carried out ranges from about 300° to about 650° C., (e.g. 400° to 650° C.), preferably from about 450° to about 600° C., and most preferably from about 500° to about 580° C.

Pressure is not critical in the dehydrocoupling process of this invention. The reaction may be carried out at subatmospheric, atmospheric, or superatmospheric pressures as desired. It will be generally preferred, however, to conduct the reaction at or near atmospheric pressure. Generally, pressures from about 1 to about 10, preferably from about 1 to about 5, and most preferably from about 1 to about 2 atmospheres can be conveniently employed.

The reaction time for the contact of the reactant with the metal oxygen composition in the present invention may be selected from a broad operable range which may vary from about 0.5 to about 10, preferably from about 1 to about 8, and most preferably from about 1 to about 4 seconds. The reaction time may be defined as the length of time in seconds which the reactant gasses measured under reaction conditions are in contact with the inorganic metal oxygen composition in the reactor. The selected reaction time may vary depending upon the reaction temperature and the desired toluene conversion level. At higher temperatures and lower toluene conversion levels, shorter contact times are required.

In addition to the toluene and/or toluene derivatives, other inert substances such as nitrogen, helium and the like may be present in the reactor. Such inert materials may be introduced to the process alone or may be combined with the other materials as feed.

Water has been found to play a significant role in the dehydrocoupling process. Higher toluene conversions and selectivities to desired products can be obtained by including water, preferably in the form of steam, in the toluene feed stream. However, care should be taken to avoid introducing too much steam, since steam cracking of the toluene can occur thereby yielding a product effluent having an undesirably high benzene and $CO_2$ by-product content. Thus, suitable steam to hydrocarbon mole ratios in the feed stream are selected in conjunction with a particular metal oxygen composition to effect improve selectivities to stilbene and diphenylethane, and toluene conversions relative to the absence of steam. Accordingly, while any effective steam-to-hydrocarbon mole ratios may be employed it is contemplated that such mole ratios constitute typically from about 0:1 to about 10:1, preferably 1:1 to about 5:1, and most preferably 2:1 to about 4:1.

The metal oxygen composition may be employed in the present invention alone or in association with a support or carrier. The use of a support may be particularly advantageous to further improve attrition resistance during reactor charging and/or under reaction conditions encountered during the course of the reaction process. Suitable supports, typically employed in spherical, tablet, or cylindrical form, for the composition are, for example, silica, alumina, silica-alumina, metal aluminates such as magnesium aluminate, calcium aluminate, titania, zirconia, activated carbon, zeolites and the like.

As noted hereinabove, the dehydrocoupling reaction may be conducted in the presence or absence of added free oxygen. When oxygen is not added to the system, that is, the reaction is conducted in the stoichiometric mode of operation, the oxygen required for the reaction is provided by the metal oxygen composition which enters into the reaction and is consequently reduced (or, in actual practice, partially reduced) during the course of the reaction. This necessitates regeneration or reoxidation which can be easily effected by heating the material in an oxygen containing gas such as air or oxygen at reaction temperatures recited herein, e.g. preferably from about 500° C. to about 600° C. for a period of time ranging from about 5 minutes to about 2 hours. In a semi-continuous operation, regeneration can be effected by periodic interruption of the reaction for reoxidation of the reduced composition, that is, periods of reaction are cycled with periods of regeneration. Operation, however, can be on a continuous basis whereby a portion of the metal oxygen composition can be continuously or intermittently removed, reoxidized and the reoxidized material can thereafter be continuously or intermittently returned to the reaction. The latter method is particularly adapted to operations in which the metal oxygen composition is fed in the form of a fluidized bed or a moving bed system.

The metal oxygen composition typically can be operated at conversions of from about 1 to about 40% and selectivities to stilbene and bibenzyl of from about 10 to about 95%, for periods of from about 5 to about 40 minutes, preferably from about 10 to about 30 minutes, and most preferably from about 20 to about 30 minutes before having to be regenerated.

When oxygen is employed as a reactant, the reaction may be conducted in either a catalytic mode of operation or a combined catalytic/stoichiometric mode of operation, depending on the amount of oxygen supplied. In the catalytic mode of operation, oxygen is supplied in an amount sufficient for the dehydrocoupling reaction. The actual amount of oxygen supplied may be specified as a function of the amount of the toluene or other suitable hydrocarbon component. On this basis the amount of oxygen supplied is ordinarily selected to provide a hydrocarbon-to-oxygen mole ratio from about 0.2:1 to about 10:1, preferably from about 0.5:1 to about 5:1, and most preferably from about 0.8:1 to about 2:1.

In the combined catalytic/stoichiometric mode of operation, the amount of oxygen supplied as a reactant is not sufficient for the dehydrocoupling reaction, thereby requiring an additional source of oxygen. The required additional oxygen will be supplied by the metal oxygen composition, that is, the composition will serve as the additional source of oxygen. As a result, the metal oxygen composition enters into the reaction and is consequently reduced during the course of the reaction. This necessitates regeneration or reoxidation of the reduced composition which can be easily effected as described hereinabove for the stoichiometric mode of operation.

In either mode of operation employing added oxygen as a reactant, whether catalytic or combined catalytic/stoichiometric, the added free oxygen may be supplied either as oxygen or an oxygen-containing gas such as air or oxygen-enriched air.

The dehydrocoupled toluene products, stilbene and bibenzyl, may be recovered and purified by any appropriate method and means known to the art. As noted previously, stilbene, of course, is the preferred product. If desired, bibenzyl can subsequently be converted to stilbene also by methods well known in the art or recycled back to the toluene coupling reactor.

The following examples are given as specific illustrations of the claimed invention. It should be understood, however, that the invention is not limited to the specific details set forth in the examples. All parts and percentages in the examples as well as in the remainder of the specification are by weight unless otherwise specified. Furthermore, while the following examples may be written in the present tense it is to be understood that such examples represent work actually performed.

In the following examples, selectively and conversion are calculated as follows:

$$\% \text{ selectivity} = \frac{\text{gms. of carbon of desired product}}{\text{gms. of carbon of feed}} \times 100$$

$$\% \text{ conversion} = \frac{\text{gms. of carbon in feed reacted}}{\text{gms. of carbon in feed}} \times 100$$

All product analysis is conducted by gas chromatography.

While the present invention is described in conjunction with the dehydrocoupling of toluene, it will be understood by those skilled in the art that methyl substituted derivatives of toluene can also be employed as the hydrocarbon feed source. Thus, the hydrocarbon feed source which can be employed in the process of the present invention comprises at least one compound represented by the structural formula

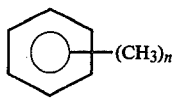
(XI)

wherein n is a number from 1 to 6, preferably 1 to 4, most preferably 1 to about 3 (e.g. 2). Representative examples of such hydrocarbon feed sources in addition to toluene, include, o-xylene, m-xylene, p-xylene, 1,3,5-trimethylbenzene, 1,2,4-trimethylbenzene, 1,2,4,6-tetramethylbenzene, hexamethylbenzene, pentamethylbenzene and the like. The most preferred toluene derivatives are the xylenes.

Generally, when a hydrocarbon feed source other than toluene is employed the dehydrocoupled product will be the appropriate methyl substituted stilbene or diphenyl ethane products, e.g. the methyl groups in excess of 1 are carried along and remain uneffected by the dehydrocoupling reactions.

The term "toluene derivative" is therefore defined herein to be at least one compound represented by formula XI wherein n is between 2 and 6.

The following examples illustrate the performance of the metal oxygen composition when operating in either the stoichiometric mode, the catalytic mode or combined catalytic/stoichiometric mode. As described above, when operating in the stoichiometric mode, the metal oxygen composition is allowed to contact with toluene, steam and nitrogen for a certain length of time during which the oxygen of the metal oxygen composition depletes due to its stoichiometric reaction with toluene in the coupling process. The metal oxygen composition, therefore, would need to be regenerated in air (or oxygen) in-situ cyclically between tests when employed commercially in this mode. Consequently, some of the runs provided herein illustrate the performance of the metal oxygen composition after regeneration.

To illustrate the performance of the metal oxygen composition when operating in the catalytic mode, said composition is allowed to contact continually with toluene, steam and air. Sufficient air is supplied in the feed to maintain the oxygen content of the composition needed for efficient dehydrogenation. Consequently, the metal oxygen composition acts as a catalyst in the toluene dehydrocoupling process and its cyclic regeneration in air is no longer necessary.

When reporting the data in Table 1, an asterisk in the column reporting toluene conversion signifies the run is within the scope of the present invention.

EXAMPLE 1

A slurry is prepared by adding 58.3 g $Sb_2O_3$, 134.0 g PbO; and 23.3 g $Bi_2O_3$ sequentially to 200 ml of isobutanol in a suitable container at room temperature. The resulting slurry is heated, stirred and refluxed at 108° C. for 24 hours to remove water as it is formed. During the reflux, the color of the slurry changes from light yellow to orange. The mixture is then cooled to room temperature (about 25° C.) filtered, and the filter cake air dried at room temperature for about 16 hours. The resulting air dried filter cake is then further dried in air at 150° C. for 48 hours in an oven. The resulting precursor composition is then calcined in air at 900° for 2 hours and sieved to a −12+20 mesh size (U.S. Sieve Series).

Forty grams of the sieved metal oxygen composition are then placed in a 20 cc stainless steel U-shaped reactor tube (O.D. ⅜", I.D. 5/16") immersed in a sand bath to supply heat to the reactor. The inlet portion of the reactor tube is horizontal, located in the sand bath, and of sufficient length to vaporize the liquid toluene and any water before it is introduced into the reactor portion. The empty heated horizontal inlet tube therefore functions as a preheating zone. The composition is then heated in the reactor tube at 450° C. while passing air through the tube at a flow rate sufficient to achieve a contact time of about 2 sec., for a period of about 16 hours to activate the composition. During activation, residual moisture and volatile impurities are removed from the metal oxygen composition and the metal oxidation states are elevated to impart optimum activity. A liquid mixture containing toluene, H₂O, and N₂ in a 1:2:1 molar ratio is then introduced into the preheating zone of the reactor tube whereupon the toluene and water are vaporized. The gaseous mixture is then passed through the remainder of the reactor tube.

The flow rate through the reactor is sufficient to achieve a contact time with the metal oxygen composition of 4.2 seconds. The temperature of the reactor during the contact is 565° C. The gaseous mixture is allowed to flow through the reactor for a period designated by "on-stream time" before product samples are removed for analysis. Several runs are conducted in series and in each run reactor effluent is scrubbed for 30 minutes with an acetone trap at 0° C. The metal oxygen composition is not regenerated between each run. Samples for analysis are removed from the reactor effluent after 0.5, 1.0, and 2.0 hours of on-stream time.

The results are summarized in Table 1 (runs 3–5) selectivity to stilbene plus diphenyl ethane (i.e., DPE) ranges from 81.7% to 84.8% at toluene conversions of 19.6% and 16.2% respectively.

EXAMPLE 2

Example 1 is repeated with the exception that the contact time between the feed gas mixture and the metal oxygen composition is reduced to 3.5 seconds, and the feed gas contains a small amount of air sufficient to provide a molar ratio between toluene-stream-N₂ and air of 1:2:1:0.87 respectively. This example is therefore conducted in the combined catalytic/stoichiometric mode. On-stream time before removing a product sample for analysis is two hours. The results are summarized at Table 1, (run 9). Selectivity to stilbene plus DPE is 72.2% at a toluene conversion of 10.3%.

EXAMPLE 3

A metal oxygen composition is prepared in accordance with Example 1 (including drying, calcination and activation conditions), and tested in accordance with the same with the exception that before each recovery run is made, the metal oxygen composition is regeneraged at reaction temperatures (560°–565° C.) by passing air through the reactor for 30 minutes at about 200 cc per minute. The results are summarized at Table 1, (runs 11 and 12). Selectivity to stilbene plus DPE ranges from 90.4% to 89.7% at respective toluene conversions of 17.3% and 15.6% with respective on-stream times of 0.5 in 1 hour.

EXAMPLE 4

The metal oxygen composition employed in this example is prepared in accordance with the procedure described in Example 1 (including drying, and activation) with the exception that the composition is calcined at 600° C. for 2 hours. 9.0 g of the metal oxygen composition are evaluated in a 5 cc micro reactor immersed in a heated salt bath at 553° C. The same feed stream employed in Example 1 is used and the contact time is controlled to be about 1.7 seconds. The catalyst is regenerated in air at 553° C. for 0.5 hours prior to each recovery run. The reactor effluent is scrubbed in dual traps at ice temperature (0° C.). Samples of reactor effluent are removed after on-stream times of 0.5, 1.0, and 2.0 hours for analysis. The results are summarized at Table 1, (runs 15–18). Selectivity to stilbene plus DPE ranges from 88.8 to 91.0% at toluene conversions at from 18.4 to 17.5% respectively.

EXAMPLE 5

The metal oxygen composition for this example is prepared in accordance with the procedures of Example 4 with the exception that the precursor composition after drying in accordance with Example 1 is placed in a ball mill jar and ball-milled for four hours. The ball mill precursor composition is then calcined at 600° C. for two hours in an oven and sieved to a mesh size of −20+40 (U.S. Series). Ball-milling is employed to improve the uniformity of the metal oxygen precursor composition. The metal oxygen composition is activated in accordance with Example 1, and tested in accordance with the procedures of Example 4. Onstream times are varied from 5 to 20 minutes and regeneration in air at 553° C. for 0.5 hours, at 2 sec. contact time is conducted before each recovery run. The results are summarized in Table 1, runs 21 to 24. Selectivity to stilbene plus DPE ranges from 85.1 to 86.9% at respective toluene conversions of 32.8 and 20.8%.

EXAMPLE 6

The metal oxygen composition prepared and tested in accordance with Example 5 (including drying, activation, and regeneration) using a feed stream comprising toluene, water and nitrogen at a molar ratio of 1:3:1 and 2 seconds contact time. Two runs are conducted with on-stream times of 20 minutes for each run. The results are summarized at Table 1, (runs 25–26). The average selectivity to stilbene plus DPE of these runs is 84.1% and an average toluene conversion of 26.1%. Comparing these results with selectivity and conversion obtained in run 24, it can be seen that the use of additional water in the feed stream improves toluene conversion substantially from 20.8% to 26.15% while the stilbene plus DPE selectivity is reduced only slightly from 86.9% to 84.1%.

EXAMPLE 7

Part A

In this example, attrition resistance of the metal oxygen composition is improved by impregnating the same with cesium hydroxide while maintaining stilbene selectivity at moderately high levels. More specifically, the metal oxygen precursor prepared in accordance with Example 1 after being dried but uncalcined is impregnated with cesium hydroxide in the following manner. In a 1-liter beaker, 2.56 g of CsOH is added to 250 cc of H₂O and the mixture is stirred to yield a uniform solution. A slurry is made by adding to this CsOH solution, 150 g of the dried metal oxide precursor. The slurry is constantly stirred while it is heated for about five hours and finally evaporated to a thick paste. The paste is dried in the oven at 150° C. for about 48 hours. The resulting metal oxygen composition slurry is boiled down to a paste and dried at 150° C. for about 48 hours. The dry composition is then calcined in air at 600° C. for two hours. The resulting calcined composition possesses the empirical formula: $Cs_{0.03}$, $Pb_{1.0}$, $SB_{0.67}$, $Bi_{0.17}$, $O_{4.5}$, and a bulk density of 2.02 g/cc.

A portion of this composition is then tested for attrition resistance in the following manner:

After sieving the composition to a mesh size of −20+40 (U.S. Series), 10 g of the composition are dropped through a 10 ft. pipe of $\frac{1}{4}''$ I.D. onto a hard surface. The particles are then sieved through a 20 mesh screen (U.S. Series) and the particles lost through the screen is between about 2 to 5%, based on the total initial weight.

The remainder of the metal oxygen composition not tested for attrition resistance is then sieved to a mesh size of $-20+40$ (U.S. Sieve Series).

Part B 10.1 g of the $-20+40$ sieved metal oxygen composition is then placed into the reactor employed in Example 1, activated for 16 hrs. in air at 450° C., 2 sec. contact time and then contacted with a vaporized feed mixture of toluene:$H_2O$:$N_2$ (1:2:1 molar ratio) which is passed through the reactor tube at 550° C. and 2 second contact time. Before recovering product for analysis, the composition is regenerated in air in accordance with Example 4. The reaction conditions and results are summarized at Table 1, run 41. The products are scrubbed in acetone traps at ice temperature and non-condensibles are collected in a sampling tube. The products are analyzed by means of gas chromatography.

The same metal oxygen composition of run 41 after regeneration and sample testing, are tested again after an additional on-stream time of 20 minutes at 512° C. reaction temperature, 2 second contact time, using a vaporized feed mixture of toluene:$H_2O$:$N_2$ (1:4:1 molar ratio). Before product recovery and analysis, the composition is regenerated in accordance with Example 4. The reaction conditions and results are summarized at Table 1, run 42.

The above procedure of run 42 is repeated again at 522° C. reaction temperature, 2 second contact time, with a vaporized feed mixture of toluene:$H_2O$:$N_2$ (1:5:1 molar ratio). The reaction conditions, and results are summarized at Table 1, run 43. As may be seen from the results of runs 41 to 43, increasing the amount of steam in the feed gas results in increased selectivity to desired products with only slight decreases in conversion upon regeneration.

Part C

To illustrate the performance of the metal oxygen composition when operating in the catalytic mode, 10.1 g of the used and regeneraged metal oxygen composition from run 43, Part B is contacted with a vaporized feed mixture of toluene:$H_2O$:air (1:4:1 molar ratio) which is continuously passed through the tube at a reaction temperature of 550° C. and 2 second contact time until a steady state is attained, i.e., about 3 hours. Product is then recovered without regeneration by the aforedescribed scrubbing procedure for an additional 20 minutes and analyzed. The reaction is then allowed to proceed until the total on-stream time is about 9 hours. At this time, the product is recovered without regeneration by the scrubbing technique and analyzed. The reaction conditions and test results are summarized at Table 1 runs 44 and 45 respectively.

As may be seen from the data of runs 44 and 45 while the conversion drops to some extent relative to the cyclic mode, the combined stilbene and DPE selectivity remains high, i.e. about 80%.

EXAMPLE 8

The metal oxygen composition of this example is prepared and tested in general accordance with the procedures described in Example 1. However, in this example 135.0 g $Bi_2O_3$ and 94.5 g ZnO are introduced into and slurried with 500 cc of isobutanol. The resulting slurry is heated and refluxed at 107.5° C. for 20 hours. The mixture is then cooled to a temperature of 25° C., filtered and the filter cake dried in an over at 110° C. for 24 hours. The dry precursor composition is then calcined at 400° C. for two hours and 800° C. for one hour in an oven. The calcined composition is then crushed and sieved to a $-12+20$ mesh size (U.S. Series) and placed in a 20 cc stainless steel reactor using a sand bath as a heat source. The composition is then activated in air at 450° C. for 16 hrs. The feed mixture of toluene, $H_2O$ and $N_2$ employed in Example 1 is then passed through the reactor which is maintained at 550° C. Contact time of the feed gas with the metal oxygen composition is 4 seconds. The reactor effluent is scrubbed in acetone for 30 minutes after each run. Two runs are conducted and samples are removed immediately after start-up and after 0.5 hours of on-stream time for analysis. In between each of these runs, the catalyst is regenerated in air at a temperature of 550° C. for a period of 0.5 hours. Results are summarized at Table 1 (runs 27-28).

EXAMPLES 9-12

A metal oxygen composition is prepared and tested in accordance with Example 4. Such composition is used to conduct several runs at varying toluene:water:$N_2$ molar ratios. Thus, in Example 9 (runs 31-32), such ratio is 1:0:1; in Example 10 (runs 33, 34, 36), 1:1:1; in Example 11 (runs 37-38), 1:2:1; and in Example 12 (runs 39-40), 1:3:1. The test conditions and results of Examples 9-12 are summarized at Table 1 (runs 31-40). The on-stream time before product analysis is taken for each of these runs is twenty minutes. Except for run 35 of Example 10, each of the runs 31 to 40 are conducted in the cyclic mode. Run 35, however, is conducted in the catalytic mode using air in place of $N_2$, but because of an obviously incorrect material balance, the products were not properly recovered and the results had to be ignored. All of runs 31 to 40 are conducted on the same metal oxygen composition, and upon completion of each run conducted in the cyclic mode the composition is regenerated in air for 0.5 hours at 553° C. prior to sample recovery. As may be seen from the data of runs 31 to 34, and 36-40, increasing the steam content substantially improves both the selectivity to desired products and conversion of toluene.

The following comparative examples are intended to illustrate the difference in results obtainable by comparing metal oxygen compositions prepared in accordance with the aqueous procedures described in the prior art. U.S. Pat. Nos. 4,091,044 and 4,254,293 are used to illustrate the aqueous preparation.

COMPARATIVE EXAMPLE 1

Example 6 of U.S. Pat. No. 4,091,044 is repeated using the same amounts of $Sb_2O_3$, PbO, and $Bi_2O_3$ employed in Example 1 (described above) with the exception that each of these components are sequentially added to 250 ml of water. The resulting slurry is heated with constant stirring and boiled down to a paste, which is then dried in an oven at 110° C. for 24 hours. The dried product possesses a light green color. A portion of the dried product is calcined at 900° C. for 2 hours and the calcined catalyst sieved to $-12+20$ mesh size (U.S. Sieve Series) for evaluation. 20 cc of the resulting mixed oxide composition are evaluated in the 20 cc stainless steel reactor tube of Example 1 using a sand bath to supply heat. Toluene, steam, and $N_2$ in a 1:2:1 molar ratio are fed through and vaporized in the reactor, said reactor being at 565° C., while controlling the flow rate to achieve a contact time of 1.4 seconds. Two runs are conducted at on-stream times of 0.5 and 1.0 hour and after each recovery run, the reactor effluent is scrubbed for 30 minutes in acetone. The metal oxygen composition is not regenerated between each of these runs. The results are summarized in Table 1 (runs 1 and 2).

COMPARATIVE EXAMPLE 2

The metal oxygen composition of this example is prepared in accordance with with the procedures of Comparative Example 1 with the exception that the composition is activated in air at 450° C. for 16 hours, 2 second contact time and evaluation of the same is conducted in accordance with the procedures of Example 1 to obtain a comparison. The results are summarized at Table 1 (runs 6-8).

COMPARATIVE EXAMPLE 3

A metal oxygen composition is prepared in accordance with the procedures of Comparative Example 2. Prior to product analysis, however, the composition is allowed to remain on-stream without regeneration prior to the recovery run for a period of 2 hours. Reactor testing procedure is conducted in accordance with the procedure of Example 2. The results are summarized at Table 1 (run 10).

COMPARATIVE EXAMPLE 4

A metal oxygen composition is prepared in accordance with Comparative Example 1 with the exception that activation is conducted in accordance with Comparative Example 2. The reactor testing and regeneration procedure is conducted in accordance with Example 3 to provide a basis of a comparison therewith. The results are summarized at Table 1 (runs 13 and 14).

COMPARATIVE EXAMPLE 5

A metal oxygen composition is prepared in accordance with the procedures of Comparative Example 1 with the exception that calcination is conducted at 600° C. for 2 hours and activation is conducted in accordance with Comparative Example 2. The resulting composition is tested in accordance with the procedures of Example 4 to provide a basis for comparison therewith. The results are summarized at Table 1 (runs 19 and 20).

COMPARATIVE EXAMPLE 6

A metal oxygen composition is prepared in accordance with U.S. Pat. No. 4,254,293 by slurrying 135.0 g $Bi_2O_3$ and 94.5 g ZnO with 500 cc of water. The resulting slurry is constantly stirred while being boiled down to a paste. The paste is then dried in an oven at 110° C. for 24 hours. The dried product is calcined at 400° C. for 2 hours and subsequently at 800° C. for 1 hour. The calcined catalyst is crushed and sieved to a $-12+20$ mesh size (U.S. Sieve Series) for evaluation. Testing of the metal oxygen composition in a 20 cc reactor is conducted in accordance with the procedures of Example 8, including activation, to provide a basis for comparison therewith. Results are summarized at Table 1 (runs 29-30).

SUMMARY OF EXAMPLES AND COMPARATIVE EXAMPLES

The following is a summary of the conclusions which can be drawn from the various examples and comparative examples provided in Table 1.

Comparing runs 3, 4 and 5 (Example 1) with runs 6, 7, and 8 (Comparative Example 2) respectively it can be seen that at comparable on-stream times metal oxygen compositions prepared by the organic method yield substantially better stilbene selectivities than metal oxygen compositions prepared by the aqueous procedure, e.g., 49.8% vs. 29.8%, 47.8% vs. 27.4% and 50.6% vs. 19.0%. Furthermore, as on-stream time increases to 2 hours the activity of the compositions prepared by the aqueous method is reduced by more than 50% (toluene conversion drops from 6.4% to 2.9%) and a major proportion of this reduction is due to a substantial drop in stilbene selectivity (i.e., selectivity drops from 29.8% to 19.0%). In contrast, the organically prepared compositions of the present invention yield only a slight drop in conversion (19.6% to 16.2%) and an increase in stilbene selectivity (i.e., 49.8% to 50.6%).

Comparing run 9 (Example 2) with run 10 (Comparative Example 3) wherein a minor quantity of air is added to the feed stream and contact time is reduced to 3.5 seconds, it can be seen that stilbene selectivity of the organically prepared compositions is higher than the aqueous preparation (i.e., 72.2% vs. 60.9%). These runs therefore illustrate the superior performance of compositions prepared by the organic method when run in the catalytic/stoichiometric mode.

Comparing runs 11 and 12 (Example 3) with runs 13 and 14 (Comparative Example 4) it can be seen that after regeneration, stilbene selectivities of runs 11 and 12 remain higher than runs 13 and 14 (i.e., 49.0% vs. 43.3%, and 49.9% vs. 44.0% at respective on-stream times of 0.5 and 1 hours).

Comparing runs 15 and 16 (Example 4) with runs 19 and 20 (Comparative Example 5) at on-stream times of 0.5 and 1.0 hour respectively and a calcination temperature of 600° C., it can be seen that stilbene selectivities, toluene conversions, and stilbene and DPE selectivities of the organically prepared compositions are for the most part substantially better than those of the aqueous prepared compositions (i.e., stilbene selectivities: 65.9% vs. 46.6%, 66.1% vs. 46.6%; toluene conversions: 18.4% vs. 6.6%, 20.2% vs. 8.6%, stilbene and DPE selectivities: 88.8% vs. 85.1%, 90.2% vs. 91.1%).

Comparing runs 27 and 28 (Example 8) with runs 29 and 30 (Comparative Example 6). It can be seen that an even greater improvement in performance of the organically prepared metal oxygen compositions is achieved using a Bi/Zn metal oxygen composition.

For example, the above noted runs yield the following comparisons:

| | |
|---|---|
| Stilbene selectivity | 28.3% vs. 11.5% |
| | 48.4% vs. 11.6% |
| Stilbene + DPE selectivity | 93.2% vs. 72.3% |
| | 92.7% vs. 77.5% |
| Toluene Conversion | 3.6% vs. 2.6% |
| | 3.1% vs. 3.4% |

TABLE 1

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | Precursor Composition Components | METAL OXYGEN COMPOSITION PREPARATION | | CALCINATION | | Feed Gas Components (molar ratio) | Contact Time of feed gas with metal oxygen comp. (Sec.) | Reaction temp (°C.) | On-Stream Time (hr) | Toluene Conversion (%) | SELECTIVITY % | | | | |
| Run No. | As Added (molar ratio) | Type | Reference Example | Temp (°C.) | Time (hr) | | | | | | Stilbene | DPE | Stilbene + DPE | Benzene | $CO + CO_2$ |
| 1 | $Sb_2O_3$:1 $PbO$:3 $Bi_2O_3$:.25 | Aq. | C. Ex. 1 | 900 | 2 | Toluene:1 Steam:2 $N_2$:1 | 1.4 | 565 | 0.5 | 6.6 | 41.4 | 30.6 | 72.0 | 18.1 | 9.0 |
| 2 | $Sb_2O_3$:1 $PbO$:3 $Bi_2O_3$:.25 | Aq. | C. Ex. 1 | 900 | 2 | Toluene:1 Steam:2 $N_2$:1 | 1.4 | 565 | 1.0 | 1.5 | 14.4 | 27.9 | 42.3 | 44.1 | 13.9 |
| 3 | $Sb_2O_3$:1 $PbO$:3 $Bi_2O_3$:.25 | Org. | Ex. 1 | 900 | 2 | Toluene:1 Steam:2 $N_2$:1 | 4.2 | 565 | 0.5 | 19.6* | 49.8 | 31.9 | 81.7 | 13.3 | 3.5 |
| 4 | $Sb_2O_3$:1 $PbO$:3 $Bi_2O_3$:.25 | Org. | Ex. 1 | 900 | 2 | Toluene:1 Steam:2 $N_2$:1 | 4.2 | 565 | 1.0 | 17.2* | 47.8 | 34.9 | 82.7 | 13.6 | 3.7(a) |
| 5 | $Sb_2O_3$:1 $PbO$:3 $Bi_2O_3$:.25 | Org. | Ex. 1 | 900 | 2 | Toluene:1 Steam:2 $N_2$:1 | 4.2 | 565 | 2.0 | 16.2* | 50.6 | 34.2 | 84.8 | 11.2 | 4.0(b) |
| 6 | $Sb_2O_3$:1 $PbO$:3 $Bi_2O_3$:.25 | Aq. | C. Ex. 2 | 900 | 2 | Toluene:1 Steam:2 $N_2$:1 | 4.2 | 565 | 0.5 | 6.4 | 29.8 | 59.2 | 89.0 | 9.6 | 1.4 |
| 7 | $Sb_2O_3$:1 $PbO$:3 $Bi_2O_3$:.25 | Aq. | C. Ex. 2 | 900 | 2 | Toluene:1 Steam:2 $N_2$:1 | 4.2 | 565 | 1.0 | 5.8 | 27.4 | 55.8 | 83.2 | 9.6 | 1.1 |
| 8 | $Sb_2O_3$:1 $PbO$:3 $Bi_2O_3$:.25 | Aq. | C. Ex. 2 | 900 | 2 | Toluene:1 Steam:2 $N_2$:1 | 4.2 | 565 | 2.0 | 2.9 | 19.0 | 57.1 | 76.1 | 20.3 | 3.6(c) |
| 9 | $Sb_2O_3$:1 $PbO$:3 $Bi_2O_3$:.25 | Org. | Ex. 2 | 900 | 2 | Toluene:1 Steam:2 $N_2$:1 Air:0.87 | 3.5 | 565 | 2 | 10.3* | 31.8 | 40.4 | 72.2 | 14.8 | 12.9(d) |
| 10 | $Sb_2O_3$:1 $PbO$:3 $Bi_2O_3$:.25 | Aq. | C. Ex. 3 | 900 | 2 | Toluene:1 Steam:2 $N_2$:1 Air:0.87 | 3.5 | 565 | 2 | 5.7 | 17.3 | 43.6 | 60.9 | 19.4 | 20.1(e) |
| 11 | $Sb_2O_3$:1 $PbO$:3 $Bi_2O_3$:.25 | Org. | Ex. 3 | 900 | 2 | Toluene:1 Steam:2 $N_2$:1 | 4.2 | 565 | 0.5 | 17.3* | 49.0 | 41.4 | 90.4 | 7.8 | 2.1(f) |
| 12 | $Sb_2O_3$:1 $PbO$:3 $Bi_2O_3$:.25 | Org. | Ex. 3 | 900 | 2 | Toluene:1 Steam:2 $N_2$:1 | 4.2 | 565 | 1.0 | 15.6* | 49.9 | 39.8 | 89.7 | 8.0 | 2.3 |
| 13 | $Sb_2O_3$:1 $PbO$:3 $Bi_2O_3$:.25 | Aq. | C. Ex. 4 | 900 | 2 | Toluene:1 Steam:2 $N_2$:1 | 4.2 | 565 | 0.5 | 11.2 | 43.3 | 49.9 | 93.2 | 6.2 | 0.7(g) |
| 14 | $Sb_2O_3$:1 $PbO$:3 $Bi_2O_3$:.25 | Aq. | C. Ex. 4 | 900 | 2 | Toluene:1 Steam:2 $N_2$:1 | 4.2 | 565 | 1.0 | 11.4 | 44.0 | 49.3 | 93.3 | 5.7 | 1.0(h) |
| 15 | $Sb_2O_3$:1 $PbO$:3 $Bi_2O_3$:.25 | Org. | Ex. 4 | 600 | 2 | Toluene:1 Steam:2 $N_2$:1 | 1.7 | 553 | 0.5 | 18.4* | 65.9 | 22.9 | 88.8 | 8.9 | 2.3 |

TABLE 1-continued

| Run No. | Precursor Composition Components As Added (molar ratio) | METAL OXYGEN COMPOSITION PREPARATION Type | Reference Example | CALCINATION Temp (°C.) | Time (hr) | Feed Gas Components (molar ratio) | Contact Time of feed gas with metal oxygen comp. (Sec.) | Reaction temp (°C.) | On-Stream Time (hr) | Toluene Conversion (%) | SELECTIVITY % Stilbene | DPE | Stilbene + DPE | Benzene | CO + CO₂ |
|---|---|---|---|---|---|---|---|---|---|---|---|---|---|---|---|
| 16 | Bi₂O₃:1 Sb₂O₃:1 PbO:3 | Org. | Ex. 4 | 600 | 2 | Toluene:1 Steam:2 N₂:1 | 1.7 | 553 | 1.0 | 20.2* | 66.1 | 24.1 | 90.2 | 7.9 | 1.9(j) |
| 17 | Bi₂O₃:.25 Sb₂O₃:1 PbO:3 | Org. | Ex. 4 | 600 | 2 | Toluene:1 Steam:2 N₂:1 | 1.7 | 553 | 1.5 | 20.7* | 68.2 | 24.1 | 92.3 | 6.0 | 1.7(j) |
| 18 | Bi₂O₃:.25 Sb₂O₃:1 PbO:3 | Org. | Ex. 4 | 600 | 2 | Toluene:1 Steam:2 N₂:1 | 1.7 | 553 | 2.0 | 17.5* | 65.0 | 26.0 | 91.0 | 7.3 | 1.8(k) |
| 19 | Bi₂O₃:.25 Sb₂O₃:1 PbO:3 | Aq. | C. Ex. 5 | 600 | 2 | Toluene:1 Steam:2 N₂:1 | 1.7 | 553 | 0.5 | 6.6 | 46.6 | 38.5 | 85.1 | 11.2 | 3.8 |
| 20 | Bi₂O₃:.25 Sb₂O₃:1 PbO:3 | Aq. | C. Ex. 5 | 600 | 2 | Toluene:1 Steam:2 N₂:1 | 1.7 | 553 | 1.0 | 8.6 | 51.0 | 40.1 | 91.1 | 7.7 | 1.3(j) |
| 21 | Bi₂O₃:.25 Sb₂O₃:1 PbO:3 | Org. | Ex. 5 | 600 | 2 | Toluene:1 Steam:2 N₂:1 | 1.7 | 553 | .0833 | 32.8* | 66.9 | 18.2 | 85.1 | 12.8 | 2.2(m) |
| 22 | Bi₂O₃:.25 Sb₂O₃:1 PbO:3 | Og. | Ex. 5 | 600 | 2 | Toluene:1 Steam:2 N₂:1 | 1.7 | 553 | .125 | 27.0* | 65.4 | 19.8 | 85.2 | 12.3 | 2.5 |
| 23 | Bi₂O₃:.25 Sb₂O₃:1 PbO:3 | Og. | Ex. 5 | 600 | 2 | Toluene:1 Steam:2 N₂:1 | 1.7 | 553 | .166 | 25.1* | 69.8 | 19.1 | 88.9 | 9.9 | 2.0 |
| 24 | Bi₂O₃:.25 Sb₂O₃:1 PbO:3 | Og. | Ex. 5 | 600 | 2 | Toluene:1 Steam:2 N₂:1 | 1.7 | 553 | .33 | 20.8* | 66.1 | 20.8 | 86.9 | 10.4 | 2.7 |
| 25 | Bi₂O₃:.25 Sb₂O₃:1 PbO:3 | Og. | Ex. 6 | 600 | 2 | Toluene:1 Steam:2 N₂:1 | 2 | 553 | .33 | 25.3* | 66.7 | 18.7 | 85.4 | 11.5 | 3.1 |
| 26 | Bi₂O₃:.25 Sb₂O₃:1 PbO:3 | Og. | Ex. 6 | 600 | 2 | Toluene:1 Steam:3 N₂:1 | 2 | 553 | .33 | 27.0* | 65.2 | 17.6 | 82.8 | 12.8 | 4.4(n) |
| 27 | Bi₂O₃:.25 Sb₂O₃:1 PbO:3 | Og. | Ex. 8 | 400 800 | 2 1 | Toluene:1 Steam:3 N₂:1 | 4 | 550 | immediate | 3.6* | 28.3 | 64.9 | 93.2 | 3.8 | 2.9 |
| 28 | Bi₂O₃:1 ZnO:4 | Og. | Ex. 8 | 400 800 | 2 1 | Toluene:1 Steam:3 N₂:1 | 4 | 550 | .5 | 3.1* | 48.4 | 44.3 | 92.7 | 4.4 | 2.9 |
| 29 | Bi₂O₃:1 ZnO:4 | Aq. | C. Ex. 6 | 400 800 | 2 1 | Toluene:1 Steam:3 N₂:1 | 4 | 550 | immediate | 2.6 | 11.5 | 60.8 | 72.3 | 12.9 | 15.0 |
| 30 | Bi₂O₃:1 | Aq. | C. Ex. 6 | 400 | 2 | Toluene:1 N₂:1 | 4 | 550 | .5 | 3.4 | 11.6 | 65.9 | 77.5 | 11.6 | 11.3 |

TABLE 1-continued

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | Precursor Composition Components | METAL OXYGEN COMPOSITION PREPARATION | | CALCINATION | | Feed Gas Components | Contact Time of feed gas with metal oxygen comp. | Reaction temp | On-Stream Time | Toluene Conversion | SELECTIVITY % | | | | |
| Run No. | As Added (molar ratio) | Type | Reference Example | Temp (°C.) | Time (hr) | (molar ratio) | (Sec.) | (°C.) | (hr) | (%) | Stilbene | DPE | Stilbene + DPE | Benzene | CO + CO$_2$ |
| | ZnO:4 | | | 800 | 1 | Steam:3 N$_2$:1 | | | | | | | | | |
| 31 | Sb$_2$O$_3$:1 PbO:3 Bi$_2$O$_3$:0.25 | Og. | Ex. 9 | 600 | 2 | Toluene:1 Steam:0 N$_2$:1 | 2 | 553 | .33 | 13.9* | 44.4 | 14.9 | 59.2 | 20.4 | 20.5(o) |
| 32 | Sb$_2$O$_3$:1 PbO:3 Bi$_2$O$_3$:0.25 | Og. | Ex. 9 | 600 | 2 | Toluene:1 Steam:0 N$_2$:1 | 2 | 553 | .33 | 9.5* | 46.0 | 23.2 | 69.2 | 13.5 | 17.2 |
| 33 | Sb$_2$O$_3$:1 PbO:3 Bi$_2$O$_3$:0.25 | Og. | Ex. 10 | 600 | 2 | Toluene:1 Steam:1 N$_2$:1 | 2 | 553 | .33 | 16.5* | 55.5 | 22.5 | 78.0 | 19.3 | 8.2 |
| 34 | Sb$_2$O$_3$:1 PbO:3 Bi$_2$O$_3$:0.25 | Og. | Ex. 10 | 600 | 2 | Toluene:1 Steam:1 N$_2$:1 | 2 | 553 | .33 | 15.4* | 53.5 | 21.2 | 74.7 | 14.2 | 11.1 |
| 35 | Sb$_2$O$_3$:1 PbO:3 Bi$_2$O$_3$:0.25 | Og. | Ex. 10 | 600 | 2 | Toluene:1 Steam:1 Air:1 | 2 | 553 | .33 | Poor Recovery | | | | | |
| 36 | Sb$_2$O$_3$:1 PbO:3 Bi$_2$O$_3$:0.25 | Og. | Ex. 10 | 600 | 2 | Toluene:1 Steam:1 N$_2$:1 | 2 | 553 | .33 | 17.2* | 55.2 | 23.7 | 78.9 | 13.0 | 8.1 |
| 37 | Sb$_2$O$_3$:1 PbO:3 Bi$_2$O$_3$:0.25 | Og. | Ex. 11 | 600 | 2 | Toluene:1 Steam:1 N$_2$:1 | 2 | 553 | .33 | 19.1* | 62.4 | 24 | 86.4 | 10.6 | 3.0 |
| 38 | Sb$_2$O$_3$:1 PbO:3 Bi$_2$O$_3$:0.25 | Og. | Ex. 11 | 600 | 2 | Toluene:1 Steam:2 N$_2$:1 | 2 | 553 | .33 | 17.6* | 61.6 | 24.2 | 85.7 | 11.0 | 3.4 |
| 39 | Sb$_2$O$_3$:1 PbO:3 Bi$_2$O$_3$:0.25 | Og. | Ex. 12 | 600 | 2 | Toluene:1 Steam:2 N$_2$:1 | 2 | 553 | .33 | 25.3* | 66.7 | 18.7 | 85.4 | 11.5 | 3.1 |
| 40 | Sb$_2$O$_3$:1 PbO:3 Bi$_2$O$_3$:0.25 | Og. | Ex. 12 | 600 | 2 | Toluene:1 Steam:3 N$_2$:1 | 2 | 553 | .33 | 27.0* | 65.2 | 17.6 | 82.8 | 12.8 | 4.4 |
| 41 | Sb$_2$O$_3$:1 PbO:3 Bi$_2$O$_3$:0.25 | Og. | Ex. 7 | 600 | 2 | Toluene:1 Steam:2 N$_2$:1 | 2 | 550 | .33 | 23.1* | 69.0 | 6.5 | 75.5 | 16.7 | 7.8(p) |
| 42 | Sb$_2$O$_3$:1 PbO:3 Bi$_2$O$_3$:0.25 | Og. | Ex. 7 | 600 | 2 | Toluene:1 Steam:4 N$_2$:1 | 2 | 512 | .33 | 15.7* | 71.5 | 14.0 | 85.5 | 11.6 | 3.0 |
| 43 | Sb$_2$O$_3$:1 PbO:3 Bi$_2$O$_3$:0.25 | Og. | Ex. 7 | 600 | 2 | Toluene:1 Steam:5 N$_2$:1 | 2 | 522 | .33 | 18.2* | 72.6 | 13.7 | 86.3 | 11.6 | 2.0 |
| 44 | Sb$_2$O$_3$:1 PbO:3 Bi$_2$O$_3$:0.25 | Og. | Ex. 7 | 600 | 2 | Toluene:1 Steam:4 Air:1 | 2 | 550 | 3.3 | 11.0* | 56.7 | 23.7 | 80.4 | 10.0 | 9.4(q) |
| 45 | Sb$_2$O$_3$:1 PbO:3 Bi$_2$O$_3$:0.25 | Og. | Ex. 7 | 600 | 2 | Toluene:1 | 2 | 550 | 9.3 | 10.6* | 53.5 | 26.9 | 80.3 | 8.6 | 11.1(r) |

TABLE 1-continued

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| Precursor Composition | METAL OXYGEN COMPOSITION PREPARATION | | CALCINATION | | Feed Gas Components (molar ratio) | Contact Time of feed gas with metal oxygen comp. (Sec.) | Reaction temp (°C.) | On-Stream Time (hr) | Toluene Conversion (%) | SELECTIVITY % | | | | |
| Components As Added (molar ratio) Run No. | Type | Reference Example | Temp (°C.) | Time (hr) | | | | | | Stilbene | DPE | Stilbene + DPE | Benzene | CO + CO$_2$ |
| PbO:3 Bi$_2$O$_3$:0.25 | | | | | Steam:4 Air:1 | | | | | | | | | |

COMMENTS
(a) no regeneration
(b) no regeneration
(c) compare runs 3, 4 & 5 with 6, 7 & 8
(d) air added to feed stream and contact time reduced
(e) compare runs 9 & 10
(f) composition regenerated with air after 0.5 hours of use and then product recovered and analyzed
(g) composition regenerated with air after 0.5 hours of use and then product recovered and analyzed
(h) compare runs 11 & 12 with runs 13 & 14
(i) regenerated
(j) regenerated
(k) regenerated
(l) compare runs 15 & 16 with runs 19 & 20
(m) metal oxygen composition of runs 21 to 24 ball milled
(n) compare runs 27 & 28 with runs 29 & 30
(o) runs 31 to 34 and 36-40 vary feed gas component ratio
(p) composition is impregnated with cesium
(q) catalytic mode
(r) catalytic mode The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a precursor metal oxygen composition capable of dehydrocoupling toluene when calcined which comprises:
   (i) reacting a mixture of metal oxides in the presence of at least one alcohol under substantially anhydrous conditions of less than about 1%, by weight water, based on the weight of organic alcohol present, said organic alcohol being present in an amount of at least 3 moles of said alcohol per mole of metal in the metal oxide mixture, the metals of said metal oxide mixture having (a) at least one member selected from the group consisting of Bi, and Pb, and (b) at least one member selected from the group consisting of Li, Na, K, Rb, Cs, Mg, Ca, Sr, Ba, Sb, Ag, Au, and Cu; and
   (ii) separating the precursor composition from the organic alcohol.

2. The process of claim 1 wherein the precursor metal oxygen composition is calcined at a temperature of from about 300° to about 1200° C.

3. The process of claim 1 wherein the precursor metal oxygen composition is calcined at a temperature of about 600° to about 900° C. and activated at a temperature of from about 350° C. to about 700° C.

4. The process of claim 1 wherein said organic alcohol is selected from the group consisting of methanol, ethanol, isopropanol, 1-propanol, isobutanol, 1-butanol, 2-butanol, t-butanol, 1-pentanol, cyclohexanol, 1-octanol, 2-octanol, 3-octanol, phenol, ethylene glycol, 1,4-butane diol, diethylene glycol, triethylene glycol, 4-methoxy butanol.

5. The process of claim 4 wherein the organic alcohol is isobutanol.

6. The process of claim 1 wherein said reaction of Step (i) is conducted by refluxing a reaction mixture comprising from about 1 to about 60%, by weight, metal oxide mixture, and from about 99 to about 40%, by weight, of at least one organic alcohol in a manner and under conditions sufficient to remove water as it forms.

7. The process of claim 6 wherein said refluxing is conducted for a period of from about 2 to about 48 hours.

8. The process of claim 1 wherein the number of moles of organic alcohol present during said reaction is at least equal to the sum of the moles of each metal oxide in the metal oxide mixture multiplied by the oxidation state of each metal in said mixture.

9. The process of claim 1 wherein the metals of said metal oxide mixture comprise Bi and Zn.

10. The process of any one of claims 1, 2, and 3 to 8, wherein the composition of said metal oxide mixture is controlled to yield a metal oxygen composition having a gram atom ratio of said metals present therein represented by the formula:

$$A_aB_bO_x$$

wherein in said formula, A and B are different and:
   (i) "A" represents at least one metal selected from the group consisting of Bi, and Pb and
   (ii) "B" represents from 1 to 3 of the metals selected from the group consisting of Li, Na, K, Rb, Cs, Mg, Ca, Sr, Ba, Sb, Ag, Au, and Cu; and
   (iii) "a" independently represents a number of about 1, "b" independently represents a number of from about 0.01 to about 100, and "x" represents a number which satisfies the average valences of metals A and B as they exist in said composition.

11. A process for preparing a metal oxygen composition capable of dehydrocoupling toluene said metal oxygen composition comprising metals having a gram atom ratio represented by the formula:

$$A_aB_bO_x$$

wherein in said formula A and B, are different and;
   (i) "A" represents at least one metal selected from the group consisting of Bi, and Pb;
   (ii) "B" represents from 1 to 3 of the metals selected from the group consisting of Li, Na, K, Rb, Cs, Mg, Ca, Sr, Ba, Sb, Ag, Au, and Cu; and
   (iii) "a" independently represents a number of about 1, "b" independently represents a number of from about 0.01 to about 100, and "x" represents a number which satisfies the average valences of metals A and B as they exist in said composition, which comprises:
   (1) admixing at least two metal oxides with at least one organic alcohol to form a reaction mixture having present therein at least 3 moles of organic alcohol per mole of metal in the metal oxide mixture, the identity and molar ratio of said metal oxides in the reaction mixture being selected to yield a gram atom relationship in accordance with said formula in the metal oxygen composition;
   (2) heating said reaction mixture to a temperature of at least 75° C. to form a metal oxygen precursor composition and water, said heating being conducted under substantially anhydrous conditions of less than about 1%, by weight water, based on the weight of the organic alcohol;
   (3) separating said precursor composition from the organic alcohol; and
   (4) calcining said precursor composition to yield said metal oxygen composition.

12. The process of claim 11 wherein the reaction mixture is a slurry which is heated at a temperature of from about 25° to about 130° C. for a period of from about 2 to about 48 hours; the metal oxygen precursor composition after separation from the reaction mixture is dried at a temperature of from about 25° to about 210° C.; and calcination is conducted in air at a temperature of from about 400° to about 1000° C. for a period of from about 0.5 to about 24 hours.

13. The process of claim 12 wherein the metal oxygen composition is calcined at a temperature of from about 600° to about 900° C.

14. The process of claim 11 wherein the organic alcohol is isobutanol.

15. A process for dehydrocoupling a hydrocarbon fees selected from toluene, toluene derivative, and mixtures thereof which comprises contacting said hydrocarbon in the vapor phase at a temperature of from about 300° to about 650° C. with a metal oxygen composition, said metal oxygen composition being prepared by the process which comprises:
(i) reacting a mixture of metal oxides in the presence of at least one organic alcohol under substantially anhydrous conditions of less than about 1%, by weight, water based on the weight of the organic alcohol present, said organic alcohol being present in an amount of at least 3 moles of said alcohol per mole of metal in the metal oxide mixture to form a metal oxygen precursor composition, the metals of said metal oxide mixture having (a) at least one member selected from the group consisting of Bi, and Pb and (b) at least one member selected from the group consisting of Li, Na, K, Rb, Cs, Mg, Ca, Sr, Ba, Sb, Ag, Au, and Cu;
(ii) separating the precursor composition from the organic alcohol; and
(iii) calcining said precursor composition.

16. The process of claim 15 wherein the contacting between said hydrocarbon and the metal oxygen composition is effected at a temperature of from about 400° to about 650° C. for a period between about 0.5 and about 10 seconds.

17. The process of claim 15 wherein steam is admixed with the hydrocarbon during said contact in an amount sufficient to provide a steam to hydrocarbon feed mole ratio of from about 1:1 to about 5:1.

18. The process of claim 15 wherein the reaction temperature is from about 500° to about 580° C.

19. The process of claim 15 wherein the dehydrocoupling reaction is conducted in a stoichiometric mode of operation in the absence of added free oxygen.

20. The process of claim 15 wherein a reactant selected from the group consisting of oxygen and an oxygen containing gas is introduced with said hydrocarbon feed.

21. The process of claim 20 wherein the oxygen and oxygen containing gas is introduced in an amount sufficient to conduct the dehydrocoupling reaction in a catalytic mode of operation.

22. The process of claim 20 wherein the oxygen and oxygen containing gas is introduced in an amount sufficient to provide a toluene to oxygen mole ratio of from about 0.2:1 to about 10:1.

23. The process of claim 20 wherein the oxygen or oxygen containing gas is introduced in an amount sufficient to conduct the dehydrocoupling reaction in a combined catalytic/stoichiometric mode of operation.

24. The process of claim 15 wherein the metal oxygen composition is admixed with a support material.

25. The process of any one of claims 15 to 24 wherein the hydrocarbon feed comprises toluene.

26. A process for preparing a precursor metal oxygen composition capable of dehydrocoupling toluene when calcined which comprises:
(i) reacting a mixture of metal oxides in the presence of at least one organic alcohol under substantially anhydrous conditions, the metals of said metal oxide mixture comprising those represented by a member selected from the group consisting of (a) at least two of Sb, Pb and Bi; of (b) Bi and Zn, to form a catalyst precursor metal oxygen composition; and
(ii) separating the precursor metal oxygen composition from said organic alcohol.

27. The process of claim 26 wherein the precursor metal oxygen composition is calcined at a temperature of from about 300° to about 1200° C.

28. The process of claim 26 wherein the precursor metal oxygen composition is calcined at a temperature of about 600° to about 900° C. and activated at a temperature of from about 350° C. to about 700° C.

29. The process of claim 26 wherein said organic alcohol is selected from the group consisting of methanol, ethanol, isopropanol, 1-propanol, isobutanol, 1-butanol, 2-butanol, t-butanol, 1-pentanol, cyclohexanol, 1-octanol, 2-octanol, 3-octanol, phenol, ethylene glycol, 1,4-butane diol, diethylene glycol, triethylene glycol, 4-methoxy butanol.

30. The process of claim 29 wherein the organic alcohol is isobutanol.

31. The process of claim 26 wherein said reaction of Step (i) is conducted by refluxing a reaction mixture comprising from about 1 to about 60%, by weight, metal oxide mixture, and from about 99 to about 40%, by weight, of at least one organic alcohol in a manner and under conditions sufficient to remove water as it forms.

32. The process of claim 31 wherein said refluxing is conducted for a period of from about 2 to about 48 hours.

33. A process for preparing a metal oxygen composition capable of dehydrocoupling toluene, said metal oxygen composition comprising metals having a gram atom ratio represented by the formula:

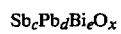

wherein "c" represents a number of about 1, "d" represents a number of from about 0.2 to about 10, "e" represents a number of from 0 to about 5, and "x" represents a number which satisfies the average valences of the metals Sb, Pb, Bi, as they exist in said composition, which comprises:
(1) admixing at least two metal oxides with at least one organic alcohol to form a reaction mixture, the identity and molar ratio of said metal oxides in the reaction mixture being selected to yield a gram atom relationship in accordance with said formula in the metal oxygen composition;
(2) heating said reaction mixture to form a metal oxygen precursor composition and water, said heating being conducted under substantially anhydrous conditions;
(3) separating said precursor composition from the organic alcohol; and
(4) calcining said precursor composition to yield said metal oxygen composition.

34. The process of claim 33 wherein the reaction mixture is a slurry which is heated at a temperature of from about 20° to about 200° C. for a period of from about 2 to about 48 hours; the metal oxygen precursor composition after separation from the reaction mixture is dried at a temperature of from about 25° to about 210° C.; and calcination is conducted in air at a temperature of from about 400° to about 1000° C. for a period of from about 0.5 to about 24 hours.

35. The process of claim 34 wherein the metal oxygen composition is calcined at a temperature of from about 600° to about 900° C.

36. The process of claim 33 wherein the organic alcohol is isobutanol.

37. A process for dehydrocoupling a hydrocarbon feed selected from toluene, toluene derivative, and mixtures thereof which comprises contacting said hydrocarbon in the vapor phase at a temperature of from about 300° to about 650° C. with a metal oxygen composition, said metal oxygen composition being prepared by the process which comprises:

(1) reacting a mixture of metal oxides in the presence of at least one organic alcohol under substantially anhydrous conditions, the metals of said metal oxide mixture comprising those represented by a member selected from the group consisting of (a) at least two of Sb, Pb, and Bi; or (b) Bi and Zn; in a manner and under conditions sufficient to form a catalyst precursor composition;

(ii) separating the precursor composition from the organic alcohol; and (iii) calcining said precursor composition.

38. The process of claim 37 wherein said metal oxygen composition is prepared in a manner sufficient to yield a gram atom ratio of said metals present therein represented by the formula:

$$Sb_cPb_dBi_eO_x$$

wherein "c" represents a number of about 1, "d" represents a number of from about 0.2 to about 10, "e" represents a number of from 0 to about 5, "x" represents a number which satisfies the average valences of the metals Sb, Pb, Bi, and they exist in said composition.

39. The process of claim 38 wherein the contacting between said hydrocarbon and the metal oxygen composition is effected at a temperature of from about 400° to about 650° C. for a period between about 0.5 and about 10 seconds.

40. The process of claim 38 wherein steam is admixed with the hydrocarbon during said contact in an amount sufficient to provide a steam to hydrocarbon feed mole ratio of from about 1:1 to about 5:1.

41. The process of claim 38 wherein the reaction temperature is from about 500° to about 580° C.

42. The process of claim 38 wherein the dehydrocoupling reaction is conducted in a stoichiometric mode of operation in the absence of added free oxygen.

43. The process of claim 38 wherein a reactant selected from the group consisting of oxygen and an oxygen containing gas is introduced with said hydrocarbon feed.

44. The process of claim 43 wherein the oxygen and oxygen containing gas is introduced in an amount sufficient to conduct the dehydrocoupling reaction in a catalytic mode of operation.

45. The process of claim 43 wherein the oxygen and oxygen containing gas is introduced in an amount sufficient to provide a toluene to oxygen mole ratio of from about 0.2:1 to about 10:1.

46. The process of claim 43 wherein the oxygen or oxygen containing gas is introduced in an amount sufficient to conduct the dehydrocoupling reaction in a combined catalytic/stoichiometric mode of operation.

47. The process of claim 38 wherein the metal oxygen composition is admixed with a support material.

48. The process of claim 38 wherein the hydrocarbon feed comprises toluene.

49. A process for preparing a metal oxygen composition capable of dehydrocoupling toluene, said metal oxygen composition comprising metals having a gram atom ratio represented by the formula:

$$D_uE_vSb_yBi_zO_x$$

wherein:

(i) "D" represents at least one member selected from the group consisting of Li, Na, K, Rb, Cs, Mg, Ca, Si, and Ba;

(ii) "E" represents at least one member selected from the group consisting of Pb, Au, Ag, and Cu; and (iii) "u" represents a number which can vary from about 0 to about 10; "v" represents a number which can vary from about 0 to about 10; "y" represents a number of which can vary from about 0.5 to about 5; "z" represents a number which can vary from about 0.01 to about 10; and "x" is a number which satisfies the average valences of metals "D", "E", Sb, and Bi, and they exist in said composition, which comprises:

(1) admixing at least two metal oxides with at least one organic alcohol to form a reaction mixture having present therein at least 3 moles of oganic alcohol per mole of metal in the metal oxide mixture, the identity and molar ratio of said metal oxides in the reaction mixture being selected to yield a gram atom relationship in accordance with said formula in the metal oxygen composition;

(2) heating said reaction mixture to form a metal oxygen precursor composition and water, said heating being conducted under substantially anhydrous conditions of less than about 1%, by weight, water, based on the weight of the organic alcohol;

(3) separating said precursor composition from the organic alcohol; and (4) calcining said precursor composition to yield said metal oxygen composition.

50. The process of claim 49 wherein the precursor metal oxygen composition is impregnated with cesium prior to calcination to improve attrition resistance of the metal oxygen composition.

51. The process of claim 49 wherein the precursor metal oxygen composition is calcined at a temperature of from about 300° to about 1200° C.

52. The process of claim 49 wherein the precursor metal oxygen composition is calcined at a temperature of about 600° to about 900° C. and activated at a temperature of from about 350° to about 700° C.

53. The process of claim 49 wherein said organic alcohol is selected from the group consisting of methanol, ethanol, isopropanol, 1-propanol, isobutanol, 1-butanol, 2-butanol, t-butanol, 1-pentanol, cyclohexanol, 1-octanol, 2-octanol, 3-octanol, phenol, ethylene glycol, 1,4-butane diol, diethylene glycol, triethylene glycol, 4-methoxy butanol.

54. The process of claim 53 wherein the organic alcohol is isobutanol.

55. The process of 49 wherein said reaction of Step (i) is conducted by refluxing a reaction mixture comprising from about 1 to about 60%, by weight, metal oxide mixture, and from about 99 to about 40%, by weight, of at least one organic alcohol in a manner and under conditions sufficient to remove water as it forms.

56. The process of claim 55 wherein said refluxing is conducted for a period of from about 2 to about 48 hours.

57. The process of claim 49 wherein the number of moles of organic alcohol present during said reaction is at least equal to the sum of the moles of each metal oxide in the metal oxide mixture multiplied by the oxidation state of each metal in said mixture.

58. The process of claim 49 wherein the reaction mixture is a slurry which is heated at a temperature of from about 20° to about 200° C. for a period of from about 2 to about 48 hours; the metal oxygen precursor composition after separation from the reaction mixture is dried at a temperature of from about 25° to about 210° C.; and calcination is conducted in air at a temperature of from about 400° to about 1000° C. for a period of from about 0.5 to about 24 hours.

59. The process of claim 58 wherein the metal oxygen composition is calcined at a temperature of from about 600° to about 900° C.

60. A process for dehydrocoupling hydrocarbon feed selected from toluene, toluene derivative, and mixtures thereof which comprises contacting said hydrocarbon in the vapor phase at a temperature of from about 300° to about 650° C. with a metal oxygen composition, said metal oxygen composition comprising metals having a gram atom ratio represented by the formula:

$$D_u E_v Sb_y Bi_z O_x$$

wherein:
(i) "D" represents at least one member selected from the group consisting of Li, Na, K, Rb, Cs, Mg, Ca, Sr, and Ba;
(ii) "E" represents at least one member selected from the group consisting of Pb, Au, Ag, and Cu; and
(iii) "u" represents a number which can vary from about 0 to about 10; "v" represents a number which can vary from about 0 to about 10; "y" represents a number which can vary from about 0.5 to about 5; "z" represents a number which can vary from about 0.01 to about 10; and "x" is a number which satisfies the average valences of metals "D", "E", Sb, and Bi, and they exist in said composition, and said metal oxygen composition being prepared by the process comprising:
(1) admixing at least two metal oxides with at least one organic alcohol to form a reaction mixture having present therein at least 3 moles of organic alcohol per mole of metal in the metal oxide mixture, the identity and molar ratio of said metal oxides in the reaction mixture being selected to yield a gram atom relationship in accordance with said formula in the metal oxygen composition;
(2) heating said reaction mixture to form a metal oxygen precursor composition and water, said heating being conducted under substantially anhydrous conditions of less than about 1%, by weight, water, based on the weight of the organic alcohol;
(3) separating said precursor composition from the organic alcohol; and
(4) calcining said precursor composition to yield said metal oxygen composition.

61. The process of claim 60 wherein the contacting between said hydrocarbon feed and the metal oxygen composition is effected at a temperature of from about 400° to about 650° C. for a period between about 0.5 and about 10 seconds.

62. The process of claim 60 wherein steam is admixed with the hydrocarbon during said contact in an amount sufficient to provide a steam to hydrocarbon feed mole ratio of from about 1:1 to about 5:1.

63. The process of claim 60 wherein the reaction temperature is from about 500° to about 580° C.

64. The process of claim 60 wherein the dehydrocoupling reaction is conducted in a stoichiometric mode of operation in the absence of added free oxygen.

65. The process of claim 60 wherein a reactant selected from the group consisting of oxygen and an oxygen containing gas is introduced with said hydrocarbon feed.

66. The process of claim 65 wherein the oxygen and oxygen containing gas is introduced in an amount sufficient to conduct the dehydrocoupling reaction in a catalytic mode of operation.

67. The process of claim 65 wherein the oxygen and oxygen containing gas is introduced in an amount sufficient to provide a toluene to oxygen mole ratio of from about 0.2:1 to about 10:1.

68. The process of claim 65 wherein the oxygen or oxygen containing gas is introduced in an amount sufficient to conduct the dehydrocoupling reaction in a combined catalytic/stoichiometric mode of operation.

69. The process of claim 60 wherein the metal oxygen composition is admixed with a support material.

70. The process of claim 60 wherein the hydrocarbon feed comprises toluene.

71. A process for preparing a precursor metal oxygen composition capable of dehydrocoupling toluene when calcined which comprises:
(i) reacting a mixture of metal oxides in the presence of at least one organic alcohol under substantially anhydrous conditions, the metals of said metal oxide mixture comprising those represented by a member selected from the group consisting of (a) Sb, Pb, and Bi, (b) Bi and Zn, (c) Pb and K, (d) Bi and Ag, (e) Au, Sb, and Bi, (f) Pb and Ba, and (g) mixtures thereof to form a catalyst precursor metal oxygen composition; and
(ii) separating the precursor metal oxygen composition from said organic alcohol.

72. The process of claim 71 wherein the precursor metal oxygen composition is calcined at a temperature of from about 300° to about 1200° C.

73. The process of claim 71 wherein the precursor metal oxygen composition is calcined at a temperature of about 600° to about 900° C. and activated at a temperature of from about 350° C. to about 700° C.

74. The process of claim 71 wherein said organic alcohol is selected from the group consisting of methanol, ethanol, isopropanol, 1-propanol, isobutanol, 1-butanol, 2-butanol, t-butanol, 1-pentanol, cyclohexanol, 1-octanol, 2-octanol, 3-octanol, phenol, ethylene glycol, 1,4-butane diol, diethylene glycol, triethylene glycol, 4-methoxy butanol.

75. The process of claim 74 wherein the organic alcohol is isobutanol.

76. The process of claim 71 wherein said reaction of Step (i) is conducted by refluxing a reaction mixture comprising from about 1 to about 60%, by weight, metal oxide mixture, and from about 99 to about 40%, by weight, of at least one organic alcohol in a manner and under conditions sufficient to remove water as it forms.

77. The process of claim 76 wherein said refluxing is conducted for a period of from about 2 to about 48 hours.

78. A process for dehydrocoupling a hydrocarbon feed selected from toluene, toluene derivative, and mixtures thereof which comprises contacting said hydrocarbon in the vapor phase at a temperature of from about 300° to about 650° C. with a metal oxygen composition, said metal oxygen composition being prepared by the process which comprises:

(1) reacting a mixture of metal oxides in the presence of at least one organic alcohol under substantially anhydrous conditions, the metals of said metal oxide mixture comprising those represented by a member selected from the group consisting of (a) Sb, Pb, and Bi, (b) Bi and Zn, (c) Pb and K, (d) Bi and Ag, (e) Au, Sb, and Bi, (f) Pb and Ba, and (g) mixtures thereof in a manner and under conditions sufficient to form a catalyst precursor composition;

(ii) separating the precursor composition from the organic alcohol; and (iii) calcining said precursor composition.

79. The process of claim 78 wherein the contacting between said hydrocarbon and the metal oxygen composition is effected at a temperature of from about 400° to about 650° C. for a period between about 0.5 and about 10 seconds.

80. The process of claim 78 wherein steam is admixed with the hydrocarbon during said contact in an amount sufficient to provide a steam to hydrocarbon feed mole ratio of from about 1:1 to about 5:1.

81. The process of claim 78 wherein the reaction temperature is from about 500° to about 580° C.

82. The process of claim 78 wherein the dehydrocoupling reaction is conducted in a stoichiometric mode of operation in the absence of added free oxygen.

83. The process of claim 78 wherein a reactant selected from the group consisting of oxygen or an oxygen containing gas is introduced with said hydrocarbon feed.

84. The process of claim 83 wherein the oxygen or oxygen containing gas is introduced in an amount sufficient to conduct the dehydrocoupling reaction in a catalytic mode of operation.

85. The process of claim 83 wherein the oxygen or oxygen containing gas is introduced in an amount sufficient to provide a toluene to oxygen mole ratio of from about 0.2:1 to about 10:1.

86. The process of claim 83 wherein the oxygen or oxygen containing gas is introduced in an amount sufficient to conduct the dehydrocoupling reaction in a combined catalytic/stoichiometric mode of operation.

87. The process of claim 78 wherein the metal oxygen composition is admixed with a support material.

88. The process of claim 78 wherein the hydrocarbon feed comprises toluene.

* * * * *